United States Patent
Blanche et al.

(10) Patent No.: US 6,485,958 B2
(45) Date of Patent: *Nov. 26, 2002

(54) METHOD FOR PRODUCING RECOMBINANT ADENOVIRUS

(76) Inventors: Francis Blanche, 41 rue des Solitaires, 75019 Paris (FR); Jean-Marc Guillaume, 42 rue Saint-Maur, 75011 Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,545
(22) PCT Filed: Jun. 20, 1997
(86) PCT No.: PCT/FR97/01107
§ 371 (c)(1), (2), (4) Date: Dec. 16, 1998
(87) PCT Pub. No.: WO98/00524
PCT Pub. Date: Jan. 8, 1998

(65) Prior Publication Data
US 2002/0028497 A1 Mar. 7, 2002

Related U.S. Application Data
(60) Provisional application No. 60/026,667, filed on Sep. 25, 1996.

(30) Foreign Application Priority Data
Jul. 1, 1996 (FR) .............................. 96 08164

(51) Int. Cl.⁷ .............................. C12N 7/02; C12N 7/01
(52) U.S. Cl. ..................................... 435/239; 435/320.1
(58) Field of Search ............................. 435/235.1, 239, 435/320.1; 424/199.1, 233.1, 93.2

(56) References Cited

U.S. PATENT DOCUMENTS

| | | | | |
|---|---|---|---|---|
| 5,837,520 A | * | 11/1998 | Shabram et al. | 435/239 |
| 6,040,174 A | * | 3/2000 | Imler et al. | 435/325 |
| 6,194,191 B1 | | 2/2001 | Zhang et al. | 435/239 |

FOREIGN PATENT DOCUMENTS

| | | |
|---|---|---|
| WO | WO 94/28152 | 12/1994 |
| WO | WO 95/19427 | 7/1995 |
| WO | WO 95/23867 | 9/1995 |
| WO | WO 95/25789 | 9/1995 |

OTHER PUBLICATIONS

Van Der Vliet, P.C., et al., "Thermolabile DNA Binding Proteins from Cells Infected with a Temperature–Sensitive Mutant of Adenovirus Defective in Viral DNA Synthesis," Journal of Virology, 15:2 pp. 348–354 (1975).

Huyghe et al., Purification of a Type 5 Recombinant Adenovirus Encoding Human p53 by Column Chromatography, Human Gene Therapy 6:1403–1416 (1995).

O'Neil et al., Virus Harvesting and Affinity–Based Liquid Chromatography, Bio/Technology 11, 173–178 (1993).

* cited by examiner

*Primary Examiner*—Mary E. Mosher
(74) *Attorney, Agent, or Firm*—Finnegan, Henderson, Farabow, Garrett, and Dunner, L.L.P.

(57) ABSTRACT

The invention concerns a method for producing recombinant adenovirus by which viral DNA is introduced in a packaging cell culture and the viruses produced are harvested after liberation in the supernatant. The invention also concerns the viruses produced and their use.

19 Claims, 17 Drawing Sheets

METHOD FOR PRODUCING RECOMBINANT ADENOVIRUS

Figure 1:
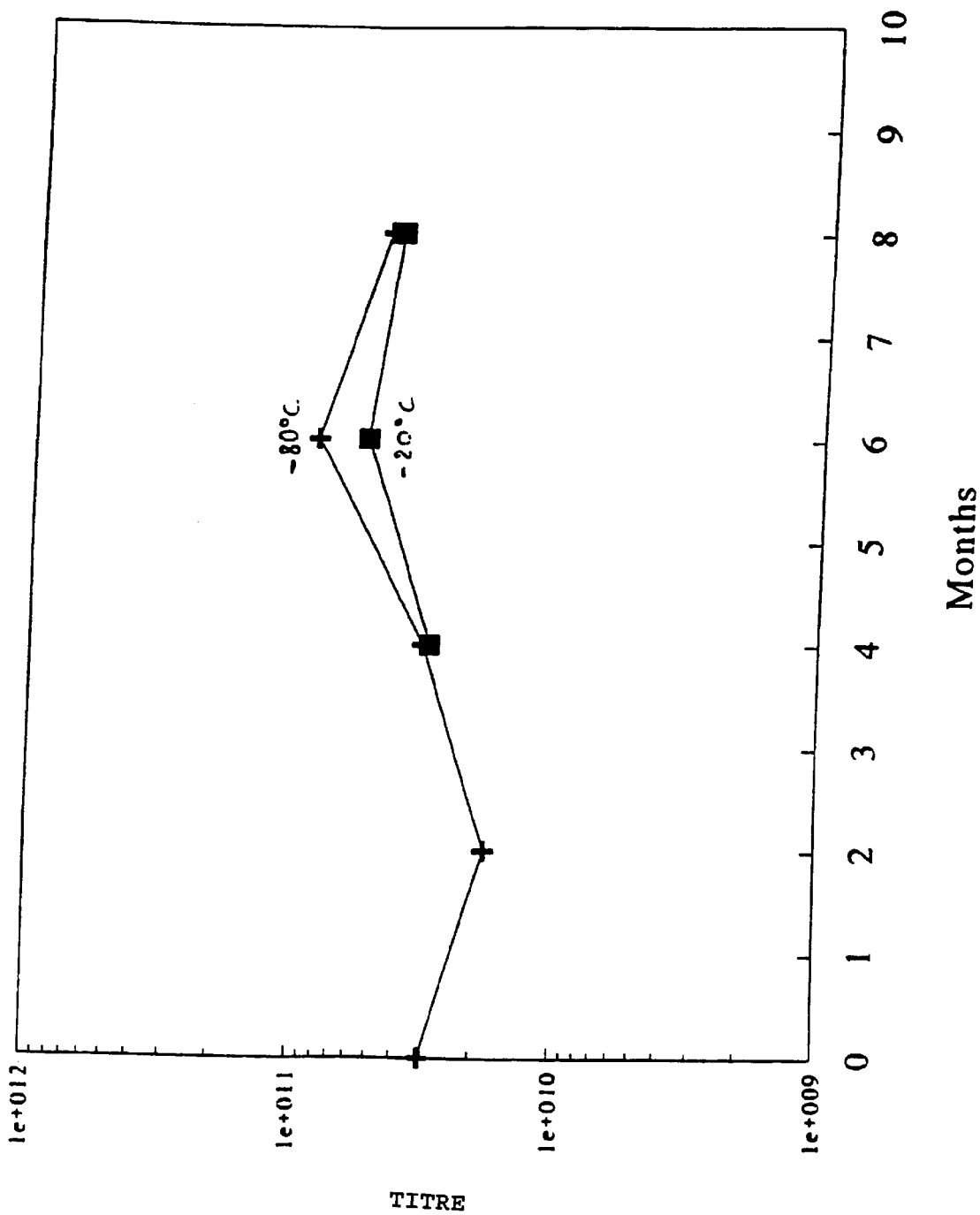

This application is a national stage application of PCT application PCT/FR97/01107 filed on Jun. 20, 1997, which claims the benefit of U.S. provisional application No. 60/026,667, filed Sep. 25, 1996, and French application FR96/08164, filed Jul. 1, 1996.

The present invention relates to a new process for the production of recombinant adenoviruses. It also relates to the purified viral preparations produced according to this process.

Adenoviruses exhibit certain properties which are particularly advantageous for use as vector for the transfer of genes in gene therapy. In particular, they have a fairly broad host spectrum, are capable of infecting quiescent cells, do not integrate into the genome of the infected cell, and have not been associated, up until now, with major pathologies in man. Adenoviruses have thus been used to transfer genes of interest into the muscle (Ragot et al., Nature 361 (1993) 647), the liver (Jaffe et al., Nature genetics 1 (1992) 372), the nervous system (Akli et al., Nature genetics 3 (1993) 224), and the like.

Adenoviruses are viruses with a linear double-stranded DNA having a size of about 36 (kilobases) kb. Their genome comprises especially an inverted repeat sequence (ITR) at each end, an encapsidation sequence (Psi), early genes and late genes. The principal early genes are contained in the E1, E2, E3 and E4 regions. Among these, the genes contained in the El region in particular are necessary for viral propagation. The principal late genes are contained in the L1 to L5 regions. The genome of the Ad5 adenovirus has been completely sequenced and is accessible on a database (see especially Genebank M73260). Likewise, parts or even the whole of other adenoviral genomes (Ad2, Ad7, Ad12 and the like) have also been sequenced.

For their use in gene therapy, various vectors derived from adenoviruses have been prepared, incorporating various therapeutic genes. In each of these constructs, the adenovirus was modified so as to render it incapable of replicating in the infected cell. Thus, the constructs described in the prior art are adenoviruses from which the El region has been deleted, which region is essential for the viral replication and at the level of which the heterologous DNA sequences are inserted (Levrero et al., Gene 101 (1991) 195; Gosh-Choudhury et al., Gene 50 (1986) 161). Moreover, to enhance the properties of the vector, it has been proposed to create other deletions or modifications in the adenovirus genome. Thus, a heat-sensitive point mutation was introduced into the ts125 mutant, making it possible to inactivate the 72 kDa DNA binding protein (DBP) (Van der Vliet et al., 1975). Other vectors comprise a deletion of another region essential for the viral replication and/or propagation, the E4 region. The E4 region is indeed involved in the regulation of the expression of the late genes, in the stability of the late nuclear RNAs, in the abolition of the expression of the host cell proteins and in the efficacy of replication of the viral DNA. Adenoviral vectors in which the E1 and E4 regions are deleted therefore possess a transcriptional background noise and an expression of viral genes which are highly reduced. Such vectors have been described for example in Applications WO 94/28152, WO 95/02697, PCT/FR96/00088). In addition, vectors carrying a modification at the level of the IVa2 gene have also been described (WO 96/10088).

The recombinant adenoviruses described in the literature are produced from different adenovirus serotypes. Indeed, various adenovirus serotypes exist whose structure and properties vary somewhat, but which exhibit a comparable genetic organization. More particularly, the recombinant adenoviruses may be of human or animal origin. As regards the adenoviruses of human origin, there may be mentioned preferably those classified in group C, in particular the adenoviruses of type 2 (Ad2), 5 (Ad5), 7 (Ad7) or 12 (Ad12). Among the various adenoviruses of animal origin, there may be mentioned preferably the adenoviruses of canine origin, and especially all the strains of the CAV2 adenoviruses [Manhattan strain or A26/61 (ATCC VR-800) for example]. Other adenoviruses of animal origin are cited especially in application WO 94/26914 incorporated into the present by reference.

In a preferred embodiment of the invention, the recombinant adenovirus is a group C human adenovirus. More preferably, it is an Ad2 or Ad5 adenovirus.

The recombinant adenoviruses are produced in an encapsidation line, that is to say a cell line capable of complementing in trans one or more functions deficient in the recombinant adenoviral genome. One of these lines is for example the line 293 into which a portion of the adenovirus genome has been integrated. More precisely, the line 293 is a human embryonic kidney cell line containing the left end (about 11–12%) of the serotype 5 adenovirus (Ad5) genome, comprising the left ITR, the encapsidation region, the E1, including E1a and E1b, region, the region encoding the pIX protein and a portion of the region encoding the pIVa2 protein. This line is capable of transcomplementing recombinant adenoviruses defective for the E1 region, that is to say lacking all or part of the E1 region, and of producing viral stocks having high titres. This line is also capable of producing, at a permissive temperature (32° C.), virus stocks comprising, in addition, the heat-sensitive E2 mutation. Other cell lines capable of complementing the E1 region have been described, based especially on human lung carcinoma cells A549 (WO 94/28152) or on human retinoblasts (Hum. Gen. Ther. (1996) 215). Moreover, the lines capable of transcomplementing several functions of the adenovirus have also been described. In particular, there may be mentioned lines complementing the E1 and E4 regions (Yeh et al., J. Virol. 70 (1996) 559; Cancer Gen. Ther. 2 (1995) 322; Krougliak et al., Hum. Gen. Ther. 6 (1995) 1575) and the lines complementing the E1 and E2 regions (WO 94/28152, WO 95/02697, WO 95/27071).

Recombinant adenoviruses are usually produced by introducing viral DNA into the encapsidation line, followed by lysis of the cells after about 2 or 3 days (kinetics of the adenoviral cycle being from 24 to 36 hours). After the lysis of the cells, the recombinant viral particles are isolated by caesium chloride gradient centrifugation.

For the carrying out of the process, the viral DNA introduced may be the complete recombinant viral genome, optionally constructed in a bacterium (WO 96/25506) or in a yeast (WO 95/03400), transfected into the cells. It may also be a recombinant virus used to infect the encapsidation line. The viral DNA may also be introduced in the form of fragments each carrying a portion of the recombinant viral genome and a zone of homology allowing, after introduction into the encapsidation cell, the viral genome to be reconstituted by homologous recombination between the various fragments. A conventional process for the production of adenoviruses thus comprises the following steps: the cells (for example the cells 293) are infected in a culture dish with a viral prestock in an amount of from 3 to 5 viral particles per cell (Multiplicity of Infection (MOI) =3 to 5), or transfected with the viral DNA. The incubation then lasts from 40 to 72 hours. The virus is then released from the nucleus by cell lysis, generally by several successive thawing cycles. The cellular lysate obtained is then centrifuged at low speed (2000 to 4000 rpm) and the supernatant (clarified cellular lysate) is then purified by centrifugation in the presence of caesium chloride in two steps:

A first rapid centrifugation of 1.5 hours on two caesium chloride layers of densities 1.25 and 1.40 flanking the virus density (1.34) so as to separate the virus from the proteins in the medium;

A second longer gradient centrifugation (from 10 to 40 hours depending on the rotor used), which constitutes the actual and sole virus purification step.

Generally, after the second centrifugation step, the virus band is predominant. Two fine, less dense bands are nevertheless observed whose examination by electron microscopy has shown that they are empty or broken viral particles in the case of the more dense band, and viral subunits (pentons, hexons) for the less dense band. After this step, the virus is harvested by piercing, using a needle, in the centrifugation tube and the caesium is removed by dialysis or desalting.

Although the purity levels obtained are satisfactory, this type of process has, nevertheless, certain disadvantages. In particular, it is based on the use of caesium chloride, which is a reactive which is incompatible with a therapeutic use in man. Because of this, it is imperative to remove the caesium chloride at the end of the purification. This process has, in addition, some other disadvantages mentioned later, which limit its use on an industrial scale.

To overcome these problems, it has been proposed to purify the virus obtained after lysis, not using a caesium chloride gradient, but by chromatography. Thus, the article by Huyghe et al. (Hum. Gen. Ther. 6 (1996) 1403) describes a study of different types of chromatographies applied to the purification of recombinant adenoviruses. This article describes especially a study of purification of recombinant adenoviruses using a weak anion-exchange chromatography (DEAE). Previous studies have already described the use of this type of chromatography for this purpose (Klemperer et al., Virology 9 (1959) 536; Philipson L., Virology 10 (1960) 459; Haruna et al., Virology 13 (1961) 264). The results presented in the article by Huyghe et al. show a fairly mediocre efficacy of the ion-exchange chromatography procedure recommended. Thus, the resolution obtained is average, the authors indicating that virus particles are present in several chromatography peaks; the yield is low (viral particle yield: 67%; infectious particle yield: 49%); and the viral preparation obtained following this chromatographic step is impure. In addition, a pretreatment of the virus with various enzymes/proteins is necessary. This same article describes, moreover, a study of the use of gel permeation chromatography, demonstrating a very poor resolution and very low yields (15–20%).

The present invention describes a new process for the production of recombinant adenoviruses. The process according to the invention results from modifications of the previous processes at the level of the production phase and/or at the level of the purification phase. The process according to the invention now makes it possible to obtain very rapidly and in an industrializable manner virus stocks in a very high quantity and quality.

One of the first aspects of the invention relates more particularly to a process for the preparation of recombinant adenoviruses in which the viruses are harvested from the culture supernatant. Another aspect of the invention relates to a process for the preparation of adenoviruses comprising an ultrafiltration step. According to another aspect, the invention also relates to a process for the purification of recombinant adenoviruses comprising an anion-exchange chromatography step. The present invention also describes an improved purification process using a gel permeation chromatography, optionally coupled to an anion-exchange chromatography. The process according to the invention makes it possible to obtain viruses of high quality, in terms of purity, stability, morphology and infectivity, with very high yields and under production conditions which are completely compatible with industrial requirements and with the legislation relating to the production of therapeutic molecules.

In particular, in terms of industrialization, the process of the invention uses methods for the treatment of culture supernatants proven on a large scale for recombinant proteins, such as microfiltration or depth filtration, and tangential ultrafiltration. Moreover, because of the stability of the virus at 37° C., this process allows a better organization at the industrial stage since, contrary to the intracellular method, the time of harvest does not need to be precise to within a half-day. Furthermore, it ensures a maximum harvesting of the virus, which is particularly important in the case of viruses defective in several regions. Moreover, the process of the invention allows easier and more precise monitoring of the kinetics of production, directly on homogeneous samples of supernatant, without pretreatment, allowing better reproducibility of the productions. The process according to the invention also makes it possible to dispense with the cell lysis step. The cell lysis has several disadvantages. Thus, it may be difficult to envisage breaking the cells by freeze-thaw cycles at the industrial level. Moreover, the alternative methods of lysis (Dounce, X-press, sonication, mechanical shearing, and the like) have disadvantages: they are potential generators of aerosols which are difficult to confine for the L2 or L3 viruses (level of confinement of the viruses, dependent on their pathogenicity or on their mode of dissemination), these viruses having, moreover, a tendency to be infectious by the aerial route; they generate shear forces and/or a heat release which are difficult to control, and which reduce the activity of the preparations. The solution of using detergents to lyse the cells would need to be validated and would require, in addition, validation of the removal of the detergent. Finally, the cell lysis leads to the presence, in the medium, of numerous cell debris which make the purification more complex. In terms of virus quality, the process of the invention potentially allows better maturation of the virus, leading to a more homogeneous population. In particular, since the packaging of the viral DNA is the last step of the viral cycle, the premature lysis of the cells potentially releases empty particles which, although non-replicative, are a priori infectious and capable of taking part in the toxic effect specific to the virus and of increasing the specific activity ratio of the preparations obtained. The specific infectivity ratio of a preparation is defined as the ratio of the total number of viral particles, measured by biochemical methods (OD260nm, CLHP, PCR, immunoenzymatic methods and the like) to the number of viral particles generating a biological effect (formation of lysis plaques on cells in culture in solid medium, transduction of cells). In practice, for a purified preparation, this ratio is determined by calculating the ratio of the concentration of the particles measured by OD at 260 nm to the concentration of plaque-forming units of the preparation. This ratio should be less than 100.

The results obtained show that the process of the invention makes it possible to obtain a virus of a purity at least equal to its homologue purified by caesium chloride gradient centrifugation, in a single step and without prior treatment, starting with a concentrated viral supernatant.

A first object of the invention therefore relates to a process for the production of recombinant adenoviruses, characterized in that the viral DNA is introduced into a culture of encapsidation cells and the viruses produced are harvested following release into the culture supernatant. Contrary to the prior processes in which the viruses are harvested following a premature cell lysis carried out mechanically or chemically, in the process of the invention, the cells are not lysed by means of an external factor. The culture is continued for a longer period, and the viruses are harvested directly in the supernatant, after simultaneous release by the encapsidation cells. The virus according to the invention is thus recovered in the cell supernatant, whereas in the prior processes, it is an intracellular, more particularly internuclear, virus.

The Applicant has now shown that, in spite of the extension of the duration of the culture and in spite of the use of larger volumes, the process according to the invention makes it possible to generate viral particles in large quantity and of better quality. In addition, as indicated above, this process makes it possible to avoid the lysis steps which are cumbersome at the industrial level and generate numerous impurities.

The principle of the process is therefore based on the harvesting of the viruses released into the supernatant. This process may involve a culture time greater than that for prior techniques based on the lysis of the cells. As indicated above, the harvesting time does not have to be precise within a half-day. It is essentially determined by the kinetics of release of the viruses into the culture supernatant.

The kinetics of release of the viruses may be monitored in various ways. In particular it is possible to use analytical methods such as RP-HPLC, IE-HPLC, semiquantitative PCR (Example 4.3), staining of dead cells with trypan blue, measurement of the release of intracellular enzymes of the LDH type, measurement of the particles in the supernatant by Coulter-type apparatus or by diffraction of light, immunological methods (ELISA, RIA, and the like) or nephelometric methods, titration by aggregation in the presence of antibodies, and the like.

Preferably, the harvesting is carried out when at least 50% of the viruses have been released into the supernatant. The time when 50% of the viruses have been released may be easily determined by drawing a kinetics according to the methods described above. Still more preferably, the harvesting is carried out when at least 70% of the viruses have been released into the supernatant. It is particularly preferable to carry out the harvesting when at least 90% of the viruses have been released into the supernatant, that is to say when the kinetics reaches a plateau. The kinetics of release of the virus is essentially based on the adenovirus replication cycle and may be influenced by certain factors. In particular, it may vary according to the type of virus used, and especially according to the type of deletion made in the recombinant viral genome. In particular, the deletion of the E3 region appears to delay the release of the virus. Thus, in the presence of the E3 region, the virus may be harvested from 24–48 hours post-infection. In contrast, in the absence of the E3 region, a higher culture time appears to be necessary. In this regard, the Applicant has performed experiments on kinetics of release of an adenovirus deficient for the E1 and E3 regions in the supernatant of the cells, and has shown that the release starts about 4 to 5 days post-infection, and lasts up to day 14 approximately. The release generally reaches a plateau between day 8 and day 14, and the titre remains stable for at least 20 days post-infection.

Preferably, in the process of the invention, the cells are cultured for a period of between 2 and 14 days. Moreover, the release of the virus may be induced by expression, in the encapsidation cell, of a protein, for example a viral protein, involved in the release of the virus. Thus, in the case of the adenovirus, the release may be modulated by expression of the Death protein encoded by the E3 region of the adenovirus (protein E3–11.6K), optionally expressed under the control of an inducible promoter. Because of this, it is possible to reduce the virus release time and to harvest, in the culture supernatant, more than 50% of the viruses 24–48 hours post-infection.

To recover the viral particles, the culture supernatant is advantageously filtered beforehand. The adenovirus having a size of about 0.1 $\mu$m (120 nm), the filtration is performed by means of membranes having a porosity sufficiently large to allow the virus to pass through, but sufficiently fine to retain the contaminants. Preferably, the filtration is carried out by means of membranes having a porosity greater than 0.2 $\mu$m. According to a particularly advantageous embodiment, the filtration is carried out by successive filtrations on membranes of decreasing porosity. Particularly good results were obtained by carrying out the filtration on depth filters of decreasing porosity 10 $\mu$m, 1.0 $\mu$m and 0.8-0.2 $\mu$m. According to another preferred variant, the filtration is carried out by tangential microfiltration on flat membranes or hollow fibres. It is possible to use, more particularly, flat Millipore membranes or hollow fibres having a porosity of between 0.2 and 0.6 $\mu$m. The results presented in the examples show that this filtration step has a yield of 100% (no loss of virus was observed by retention on the filter having the lowest porosity).

According to another aspect of the invention, the Applicant has now developed a process which makes it possible to harvest and purify the virus from the supernatant. To this effect, the supernatant thus filtered (or clarified) is subjected to ultrafiltration. This ultrafiltration makes it possible (i) to concentrate the supernatant, the volumes involved being large, (ii) to carry out a first purification of the virus and (iii) to adjust the preparation buffer to the subsequent preparation steps. According to a preferred embodiment, the supernatant is subjected to tangential ultrafiltration. Tangential ultrafiltration consists in concentrating and fractionating a solution between two compartments, retentate and filtrate, separated by membranes with a determined cut-off, by creating a flow in the retentate compartment of the device and by applying a transmembrane pressure between this compartment and the filtrate compartment. The flow is generally produced by means of a pump in the retentate compartment of the device and the transmembrane pressure is controlled by means of a valve on the liquid stream of the retentate circuit or a variable capacity pump on the liquid stream of the filtrate circuit. The speed of flow and the transmembrane pressure are chosen so as to generate low shear forces (reynolds number less than 5000 sec$^{-1}$, preferably less than 3000 sec$^{-1}$, pressure less than 1.0 bar) while avoiding blocking of the membranes. Various systems may be used to carry out the ultrafiltration, such as for example spiral membranes (Millipore, Amicon), flat membranes or hollow fibres (Amicon, Millipore, Sartorius, Pall, GF, Sepracor). The adenovirus having a mass of about 1000 kDa, membranes having a cut-off of less than 1000 kDa, preferably of between 100 kDa and 1000 kDa, are advantageously used within the framework of the invention. The use of membranes having a cut-off of 1000 kDa or greater indeed causes a substantial loss of virus at this stage. Preferably, membranes having a cut-off of between 200 and 600 kDa, still more preferably between 300 and 500 kDa, are used. The experiments presented in the examples show that the use of a membrane having a cut-off of 300 kDa allows the retention of more than 90% of the viral particles while removing contaminants from the medium (DNA, proteins in the medium, cellular proteins and the like). The use of a cut-off of 500 kDa offers the same advantages.

The results presented in the Examples show that this step makes it possible to concentrate large volumes of supernatant, without loss of virus (yield of 90%), and that it generates a virus of better quality. In particular, concentration factors of 20 to 100 fold can be easily obtained.

This ultrafiltration step thus constitutes an additional purification compared with the conventional scheme since the contaminants with a mass less than the cut-off (300 or 500 kDa) are removed, at least in part. The enhancement of the quality of the viral preparation is clear when the aspect of the separation is compared after the first ultracentrifugation step according to the two processes. In the conventional process involving lysis, the tube of viral preparation has a cloudy appearance with a coagulum (lipids, proteins) which sometimes touches the virus band, whereas in the process of the invention, the preparation after release and ultrafiltration has a band which is already well resolved from the contaminants in the medium which persist in the top phase. The enhancement of the quality is also demonstrated when a comparison is made of the ion-exchange chromatography profiles of a virus obtained by cell lysis relative to the virus obtained by ultrafiltration as described in the present invention. Moreover, it is possible to further enhance the quality by pursuing the ultrafiltration by diafiltration of the concentrate. This diafiltration is carried out on the same principle as the tangential ultrafiltration, and makes it possible to remove more completely the contaminants of size greater than the membrane cut-off, while equilibrating the concentrate in the purification buffer.

Moreover, the Applicant has also shown that this ultrafiltration then makes it possible to purify the virus directly by chromatography on an ion-exchange column or by gel permeation chromatography, making it possible to obtain an excellent resolution of the viral particle peak without a need for treating the preparation prior to the chromatography. This is particularly unexpected and advantageous. Indeed, as indicated in the article by Hyughe et al., cited above, the chromatographic purification of viral preparations gives mediocre results and further requires a pretreatment of the viral suspension with Benzonase and cyclodextrins.

More particularly, the process according to the invention is therefore characterized in that the viruses are harvested by ultrafiltration.

As indicated above, the resulting concentrate can be used directly for purification of the virus. This purification may be carried out by previous conventional techniques such as centrifugation on a caesium chloride gradient or another ultracentrifugation medium allowing the particles to be separated according to their size, density or sedimentation coefficient. The results presented in Example 4 show, indeed, that the virus thus obtained has remarkable characteristics. In particular, according to the invention, it is possible to replace the caesium chloride with a solution of iodixanol, 5,5'-[(2-hydroxy-1,3-propanediyl)bis (acetylimino)]-bis[N,N'-bis(2,3-dihydroxypropyl)-2,4,6-triiodo-1,3-benzenedicarboxamide] in which the virus sediments at equilibrium at a relative density of between 1.16 and 1.24. The use of this solution is advantageous because, unlike caesium chloride, it is not toxic. Moreover, the Applicant has also shown that, advantageously, the concentrate obtained also makes it possible to purify the virus directly by an ion-exchange mechanism or by gel permeation, and to obtain an excellent resolution of the viral particle chromatographic peak without the need for pretreatment.

According to a preferred embodiment, the viruses are therefore harvested and purified by anion-exchange chromatography.

For the anion-exchange chromatography, various types of supports may be used, such as cellulose, agarose (Sepharose gels), dextran (Sephadex gels), acrylamide (Sephacryl gels, Trisacryl gels), silica (TSK gels-SW gel), poly[styrene-divinylbenzene] (Source gels or Poros gels), ethyleneglycol-methacrylate copolymer (Toyopearl HW gels and TSK gels-PW gel), or mixtures (agarose-dextran: Superdex gel). Moreover, to enhance the chromatographic resolution, it is preferable, within the framework of the invention, to use supports in the form of beads, having the following characteristics:

as spherical as possible, of calibrated diameter (beads which are all identical or which are as homogeneous as possible), without imperfections or breaks, with the smallest possible diameter: beads of 10 $\mu$m have been described (MonoBeads from Pharmacia or TSK gel from TosoHaas, for example). This value appears to constitute the lower limit for the diameter of beads whose porosity should, moreover, be very high in order to allow penetration of the objects to be chromatographed inside the beads (see below), while remaining rigid in order to withstand pressure.

Moreover, to chromatograph the adenoviruses which constitute objects of very large size (diameter >100 nm), it is important to use gels having a high upper limit of porosity, or even as high as possible, so as to allow access of the viral particles to the functional groups with which they have to interact.

Advantageously, the support is chosen from agarose, dextran, acrylamide, silica, poly[styrene-divinylbenzene], ethyleneglycol-methacrylate copolymer, alone or as a mixture.

For the anion-exchange chromatography, the support used should be functionalized by grafting a group capable of interacting with an anionic molecule. Most generally, the group consists of an amine which may be ternary or quaternary. By using a ternary amine, such as DEAE for example, a weak anion exchanger is obtained. By using a quaternary amine, a strong anion exchanger is obtained.

Within the framework of the present invention, it is particularly advantageous to use a strong anion exchanger. Thus, a chromatographic support as indicated above, functionalized by quaternary amines, is preferably used according to the invention. Among the supports functionalized by quaternary amines, there may be mentioned, as examples, the resins Source Q, Mono Q, Q Sepharose, Poros HQ and Poros QE, resins of the Fractogel TMAE type, and the Toyopearl Super Q resins.

Preferred examples of resins which can be used within the framework of the invention are the Source, especially Source Q, such as 15 Q (Pharmacia), the MonoBeads, such as Q (Pharmacia), the Poros HQ and Poros QE type resins. The MonoBeads support (diameter of the beads 10±0.5 $\mu$m) has been commercially available for more than 10 years and the resins of the Source (15 $\mu$m) or Poros (10 $\mu$m or 20 $\mu$m) type for about 5 years. The latter two supports exhibit the advantage of having a very broad internal pore distribution (they range from 20 nm to 1 $\mu$m), thus allowing the passage of very large objects through the beads. Furthermore, they offer very little resistance to the circulation of liquid through the gel (therefore very little pressure) and are very rigid. The transport of solutes towards the functional groups with which they will interact is therefore very rapid. The Applicant has shown that these parameters are particularly important in the case of the adenovirus, whose diffusion is slow because of its size.

The results presented in the Examples show that the adenovirus may be purified from the concentrate in a single anion-exchange chromatography step, that the purification yield is excellent (140% in terms of tdu, compared with the value of 49% reported by Huyghes et al.) and that the resolution is excellent. In addition, the results presented show that the adenovirus obtained has a high infectivity, and therefore possesses the characteristics required for a therapeutic use. Particularly advantageous results were obtained with a strong anion exchanger, that is to say functionalized by quaternary amines, and especially with the resin Source Q. The resin Source Q15 is particularly preferred.

In this regard, another subject of the invention relates to a process for the purification of recombinant adenoviruses from a biological medium characterized in that it comprises a step of purification by strong anion-exchange chromatography.

According to this variant, the biological medium may be a supernatant of encapsidation cells producing the said virus, a lysate of encapsidation cells producing the said virus, or a prepurified solution of the said virus.

Preferably, the chromatography is carried out on a support functionalized with a quaternary amine. Still according to a preferred mode, the support is chosen from agarose, dextran, acrylamide, silica, poly[styrene-divinylbenzene], ethyleneglycol-methacrylate copolymer, alone or as a mixture.

A particularly advantageous embodiment is characterized in that the chromatography is performed on a Source Q resin, preferably Q15.

Moreover, the process described above is advantageously carried out using a supernatant of producing cells, and comprises a preliminary ultrafiltration step. This step is advantageously carried out under the conditions defined above, and in particular, it is a tangential ultrafiltration on a membrane having a cut-off of between 300 and 500 kDa.

According to another embodiment of the process of the invention, the viruses are harvested and purified by gel permeation chromatography.

The gel permeation may be performed directly on the supernatant, on the concentrate, or on the virus derived from the anion-exchange chromatography. The supports mentioned for the anion-exchange chromatography may be used in this step, but without functionalization.

In this regard, the preferred supports are agarose (Sepharose gels), dextran (Sephadex gels), acrylamide (Sephacryl gels, Trisacryl gels), silica (TSK gels-SW gel), ethyleneglycol-methacrylate copolymer (Toyopearl HW gels and TSK gels-PW gel), or mixtures (agarose-dextran: Superdex gel). Particularly preferred supports are:

Superdex 200HR (Pharmacia)
Sephacryl S-500HR, S-1000HR or S-2000 (Pharmacia)
TSK G6000 PW (TosoHaas).

A preferred process according to the invention therefore comprises an ultrafiltration followed by an anion-exchange chromatography.

Another preferred process comprises an ultrafiltration followed by an anion-exchange chromatography, followed by a gel permeation chromatography.

Another variant of the invention relates to a process for the purification of adenoviruses from a biological medium comprising a first step of ultracentrifugation, a second step of dilution or dialysis, and a third step of anion-exchange chromatography. Preferably, according to this variant, the first step is performed by rapid ultracentrifugation on a caesium chloride gradient. The term rapid means an ultracentrifugation ranging from about 0.5 to 4 hours. During the second step, the virus is diluted or dialysed against buffer, in order to facilitate its injection onto the chromatography gel, and the elimination of the ultracentrifugation medium. The third step is performed using an anion, preferably strong anion, exchange chromatography as described above. In a typical experiment, starting with the virus harvested in the supernatant (or optionally intracellular), a 1st rapid ultracentrifugation is performed with caesium chloride (as in Example 3). Next, after a simple dilution of the sample (for example with 10 volumes of buffer) or after a simple dialysis in buffer, the sample is subjected to ion-exchange chromatography (as in Example 5.1.). The advantage of this variant of the process of the invention comes from the fact that it uses 2 totally different modes of separation of the virus (density and surface charge), which may possibly bring the virus to a level of quality combining the performances of the 2 methods. In addition, the chromatography step makes it possible to remove simultaneously the medium used for the ultracentrifugation (caesium chloride for example, or any other equivalent medium mentioned above).

Another subject of the invention relates to the use of iodixanol, 5,5'-[(2-hydroxy-1,3-propanediyl)bis (acetylimino)]bis[N,N'-bis(2,3-dihydroxypropyl)-2,4,6-triiodo-1,3-benzenedicarboxamide] for the purification of adenoviruses.

For carrying out the process of the invention, various adenovirus encapsidation cells may be used. In particular, the encapsidation cells may be prepared from various pharmaceutically utilizable cells, that is to say cultivatable under industrially acceptable conditions and not having a recognized pathogenic character. They may be established cell lines or primary cultures and especially human retinoblasts, human lung carcinoma cells, or embryonic kidney cells. They may be advantageously cells of human origin which can be infected by an adenovirus. In this regard, there may be mentioned the KB, Hela, 293, Vero, gmDBP6, HER, A549, HER cells and the like.

The cells of the KB line are derived from a human epidermal carcinoma. They are accessible at the ATCC (ref. CCL17) as well as the conditions allowing their culture. The human cell line Hela is derived from a human epithelium carcinoma. It is also accessible at the ATCC (ref. CCL2) as well as the conditions allowing its culture. The line 293 cells are human embryonic kidney cells (Graham et al., J. Gen. Virol. 36 (1977) 59). This line contains especially, integrated in its genome, the left part of the genome of the human adenovirus Ad5 (12%). The cell line gm DBP6 (Brough et al., Virology 190 (1992) 624) consists of Hela cells carrying the adenovirus E2 gene under the control of the MMTV LTR.

They may also be cells of canine origin (BHK, MDCK, and the like). In this regard, the cells of the canine line MDCK are preferred. The conditions for the culture of the MDCK cells have been described especially by Macatney et al., Science 44 (1988) 9.

Various encapsidation cell lines have been described in the literature and are mentioned in the Examples. They are advantageously cells which transcomplement the adenovirus E1 function. Still more preferably, they are cells which transcomplement the adenovirus E1 and E4 or E1 and E2a functions. These cells are preferably derived from the human embryonic cells of the kidney or the retina, or human lung carcinomas.

The invention thus provides a process for the production of particularly advantageous recombinant adenoviruses. This process is suited to the production of recombinant viruses which are defective for one or more regions, and in particular of viruses defective for the E1 region, or for the E1 and E4 regions. Moreover, it is applicable to the production of adenoviruses of various serotypes, as indicated above.

According to a particularly advantageous mode, the process of the invention is used for the production of recombinant adenoviruses in which the E1 region is inactivated by deletion of a PvuII-BglII fragment stretching from nucleotide 454 to nucleotide 3328, in the Ad5 adenovirus sequence. This sequence is accessible in the literature and also on a database (see especially Genebank No. M/3260). In another preferred embodiment, the E1 region is inactivated by deletion of an HinfII-Sau3A fragment stretching from nucleotide 382 to nucleotide 3446. In a specific mode, the process allows the production of vectors comprising a deletion of the whole of the E4 region. This may be carried out by excision of an MaeII-MscI fragment corresponding to nucleotides 35835-32720. In another specific mode, only a functional part of E4 is deleted. This part comprises at least the ORF3 and ORF6 frames. By way of example, these coding frames can be deleted from the genome in the form of PvuII-AluI and BglII-PvuII fragments respectively, corresponding to nucleotides 34801-34329 and 34115-33126 respectively. The deletions of the E4 region of the virus Ad2 dl808 or of the viruses Ad5 dl1004, Ad5 dl1007, Ad5 dl1011 or Ad5 dl1014 can also be used within the framework of the invention. In this regard, the cells of the invention are particularly advantageous for the production of viruses comprising an inactive E1 region and a deletion in the E4 region of the type present in the genome of AdS dl1014, that is to say of E4-viruses conserving the reading frame ORF4.

As indicated above, the deletion in the E1 region covers advantageously all or part of the E1A and E1B regions. This deletion should be sufficient to render the virus incapable of autonomous replication in a cell. The part of the E1 region which is deleted in the adenoviruses according to the invention advantageously covers nucleotides 454-3328 or 382-3446.

The positions given above refer to the wild-type Ad5 adenovirus sequence as published and accessible on a database. Although minor variations may exist between the various adenovirus serotypes, these positions are generally applicable to the construction of recombinant adenoviruses according to the invention from any serotype, and especially the adenoviruses Ad2 and Ad7.

Moreover, the adenoviruses produced may possess other alterations in their genome. In particular, other regions may be deleted in order to increase the capacity of the virus and reduce its side effects linked to the expression of viral genes. Thus, all or part of the E3 or IVa2 region in particular may be deleted. As regards the E3 region, it may however be particularly advantageous to conserve the part encoding the gp19K protein. This protein indeed makes it possible to prevent the adenoviral vector from becoming the subject of an immune reaction which (i) would limit its action and (ii) could have undesirable side effects. According to a specific mode, the E3 region is deleted and the sequence encoding the gp19K protein is reintroduced under the control of a heterologous promoter.

As indicated above, adenoviruses constitute vectors for the transfer of genes which are very efficient for gene and cell therapy applications. For that, a heterologous nucleic acid sequence whose transfer and/or expression into a cell, an organ or an organism is desired may be inserted into their genome. This sequence may contain one or more therapeutic genes, such as a gene whose transcription and possible translation in the target cell generate products having a therapeutic effect. Among the therapeutic products, there may be mentioned more particularly enzymes, blood derivatives, hormones, lymphokines: interleukins, interferons, TNF and the like (FR 9203120), growth factors, neurotransmitters or their precursors or synthesis enzymes, trophic factors: BDNF, CNTF, NGF, IGF, GMF, aFGF, bFGF, NT3, NT5 and the like; apolipoproteins: ApoAI, ApoAIV, ApoE and the like (WO 94/25073), dystrophin or a minidystrophin (WO 93/06223), tumour suppressor genes: p53, Rb, Rap1A, DCC, k-rev and the like (WO 94/24297), genes encoding factors involved in coagulation: factors VII, VIII, IX and the like, suicide genes: thymidine kinase, cytosine deaminase and the like, or alternatively all or part of a natural or artificial immunoglobulin (Fab, ScFv and the like, WO 94/29446), and the like. The therapeutic gene may also be an antisense gene or sequence, whose expression in the target cell makes it possible to control the expression of genes or the transcription of cellular mRNAs. Such sequences can for example be transcribed, in the target cell, into RNAs which are complementary to cellular mRNAs and can thus block their translation into protein, according to the technique described in Patent EP 140 308. The therapeutic gene may also be a gene encoding an antigenic peptide, capable of generating an immune response in man, for the production of vaccines. They may be especially antigenic peptides specific for the Epstein-Barr virus, the HIV virus, the hepatitis B virus (EP 185 573), the pseudorabies virus, or specific for tumours (EP 259 212).

Generally, the heterologous nucleic acid sequence also comprises a transcription promoter region which is functional in the infected cell, as well as a region situated in 3' of the gene of interest, and which specifies a transcriptional end signal and a polyadenylation site. All of these elements constitute the expression cassette. As regards the promoter region, it may be a promoter region which is naturally responsible for the expression of the considered gene when the said promoter region is capable of functioning in the infected cell. It may also be regions of different origin (which are responsible for the expression of other proteins, or which are even synthetic). In particular, they may be promoter sequences of eukaryotic or viral genes or any promoter or derived sequence, stimulating or repressing the transcription of a gene in a specific manner or otherwise and in an inducible manner or otherwise. By way of example, they may be promoter sequences derived from the genome of the cell which it is desired to infect, or of the genome of a virus, especially the promoters of the adenovirus MLP, E1A genes, the RSV-LTR, CMV promoter, and the like. Among the eukaryotic promoters, there may also be mentioned the ubiquitous promoters (HPRT, vimentin, α-actin, tubulin and the like), the promoters of the intermediate filaments (desmin, neurofilaments, keratin, GFAP and the like), the promoters of therapeutic genes (MDR, CFTR, factor VIII type and the like), the tissue-specific promoters (pyruvate kinase, villin, the promoter for the intestinal fatty acid-binding protein, the promoter for α-actin of the smooth muscle cells, promoters specific for the liver; Apo AI, Apo AII, human albumin and the like) or alternatively the promoters which respond to a stimulus (steroid hormone receptor, retinoic acid receptor and the like). In addition these expression sequences may be modified by the addition of activating or regulatory sequences or of sequences allowing a tissue-specific or predominant expression. Moreover, when the inserted nucleic acid does not contain expression sequences, it may be inserted into the genome of the defective virus downstream of such a sequence.

Moreover, the heterologous nucleic acid sequence may also contain, in particular upstream of the therapeutic gene, a signal sequence directing the synthesized therapeutic product in the secretory pathways of the target cell. This signal sequence may be the natural signal sequence for the therapeutic product, but it may also be any other functional signal sequence or an artificial signal sequence.

The expression cassette for the therapeutic gene may be inserted into various sites of the genome of the recombinant adenovirus, according to the techniques described in the prior art. It can first of all be inserted at the level of the E1 deletion. It can also be inserted at the level of the E3 region, as an addition or as a substitution of sequences. It can also be located at the level of the deleted E4 region.

The present invention also relates to the purified viral preparations obtained according to the process of the invention, as well as any pharmaceutical composition comprising one or more defective recombinant adenoviruses prepared according to this process. The pharmaceutical compositions of the invention can be formulated for a topical, oral, parenteral, intranasal, intravenous, intramuscular, subcutaneous, intraocular or transdermal administration and the like.

Preferably, the pharmaceutical composition contains vehicles which are pharmaceutically acceptable for an injectable formulation. These may be in particular saline (monosodium or disodium phosphate, sodium, potassium, calcium or magnesium chloride and the like, or mixtures of such salts), sterile or isotonic solutions, or dry, especially freeze-dried, compositions which, upon addition depending on the case of sterilized water or physiological saline, allow the constitution of injectable solutions. Other excipients can be used, such as, for example a hydrogel. This hydrogel can be prepared from any biocompatible and noncytotoxic polymer (homo or hetero). Such polymers have for example been described in Application WO 93/08845. Some of them, such as especially those obtained from ethylene and/or propylene oxide, are commercially available. The virus doses used for the injection can be adjusted according to various parameters, and especially according to the mode of administration used, the relevant pathology, the gene to be expressed, or the desired duration of treatment. In general, the recombinant adenoviruses according to the invention are formulated and administered in the form of doses of between $10^4$ and $10^{14}$ pfu, and preferably $10^6$ to $10^{10}$ pfu. The term pfu (plaque forming unit) corresponds to the infectivity of an adenovirus solution, and is determined by infecting an appropriate cell culture and measuring, generally after 15 days, the number of infected cell plaques. The techniques for determining the pfu titre of a viral solution are well documented in the literature.

Depending on the therapeutic gene, the viruses thus produced can be used for the treatment or the prevention of numerous pathologies, including genetic diseases (dystrophy, cystic fibrosis and the like), neurodegenerative diseases (Alzheimer, Parkinson, ALS and the like), cancers, pathologies linked to coagulation disorders or to dyslipoproteinaemias, pathologies linked to viral infections (hepatitis, AIDS and the like), and the like.

The present invention will be more fully described with the aid of the following examples which should be considered as illustrative and nonlimiting.

Legend to the figures

FIG. 1: Study of the stability of the adenovirus purified according to Example 4.

Figure 2:
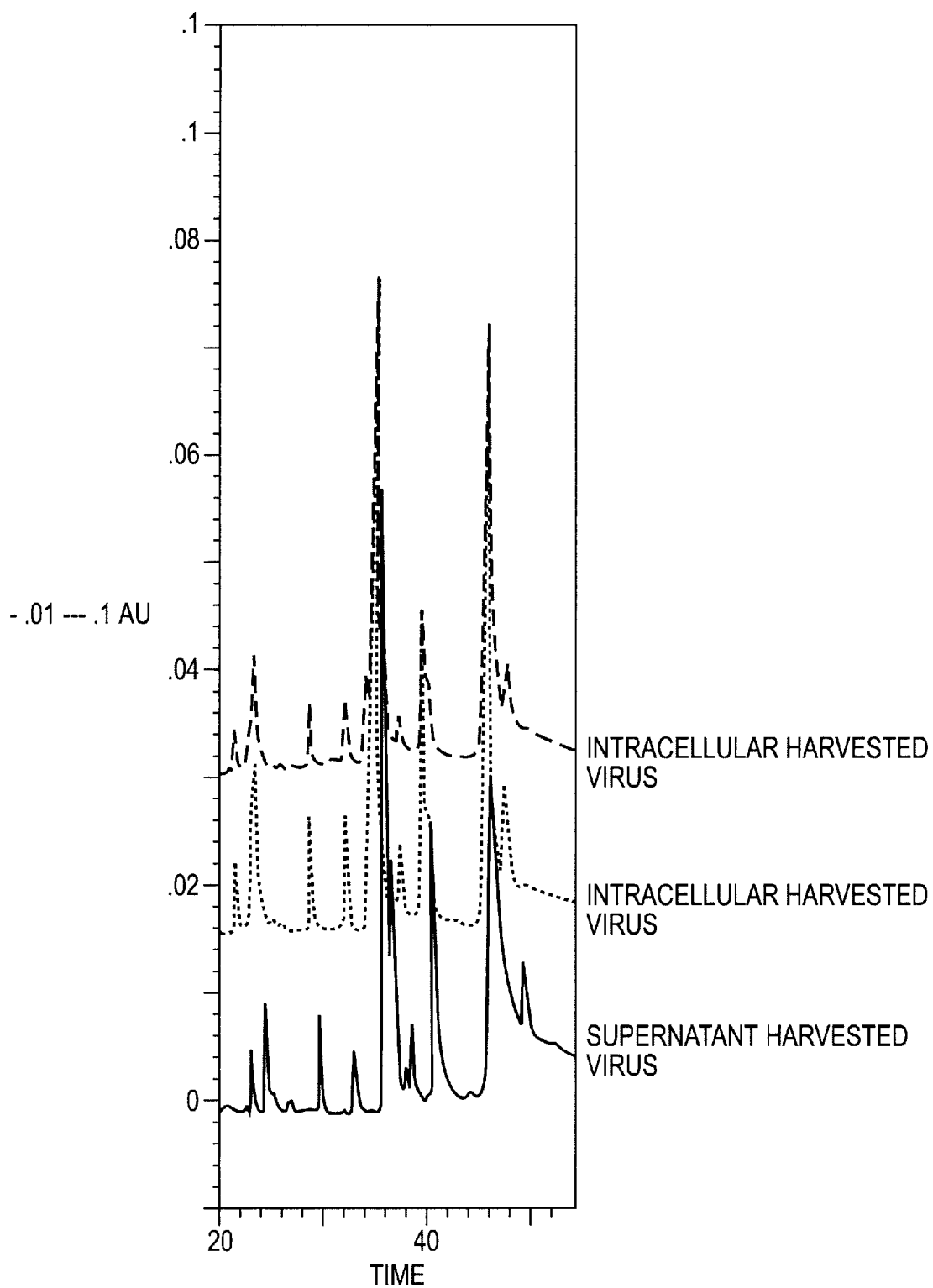

FIG. 2: HPLC (reversed phase) analysis of the adenovirus purified according to Example 4. Comparison with the adenovirus of Example 3.

Figure 3:
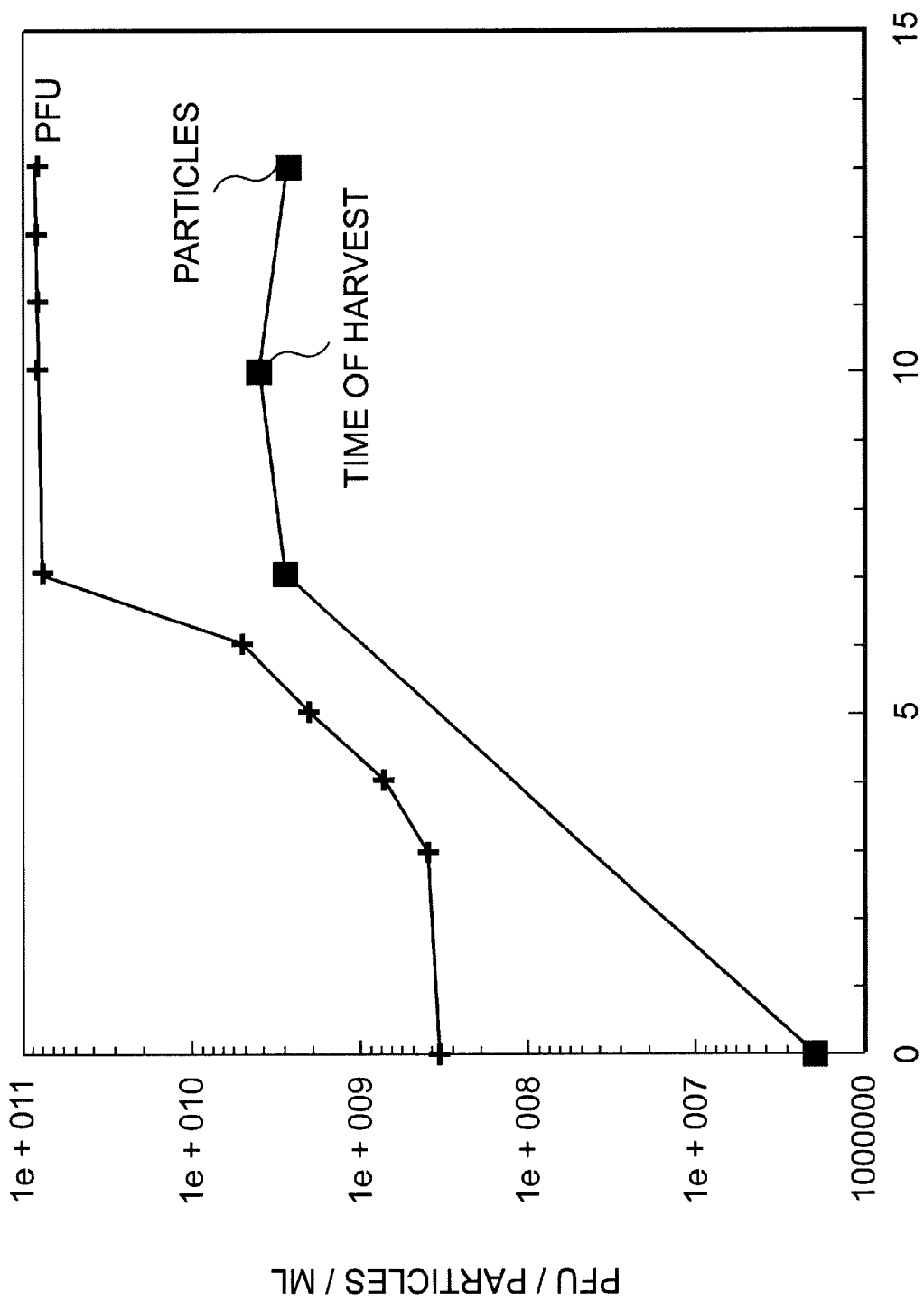

FIG. 3: Kinetics of release of the adenovirus Ad-βGal in the supernatant of cells 293, measured by semiquantitative PCR and Plaque Assay.

Figure 4:
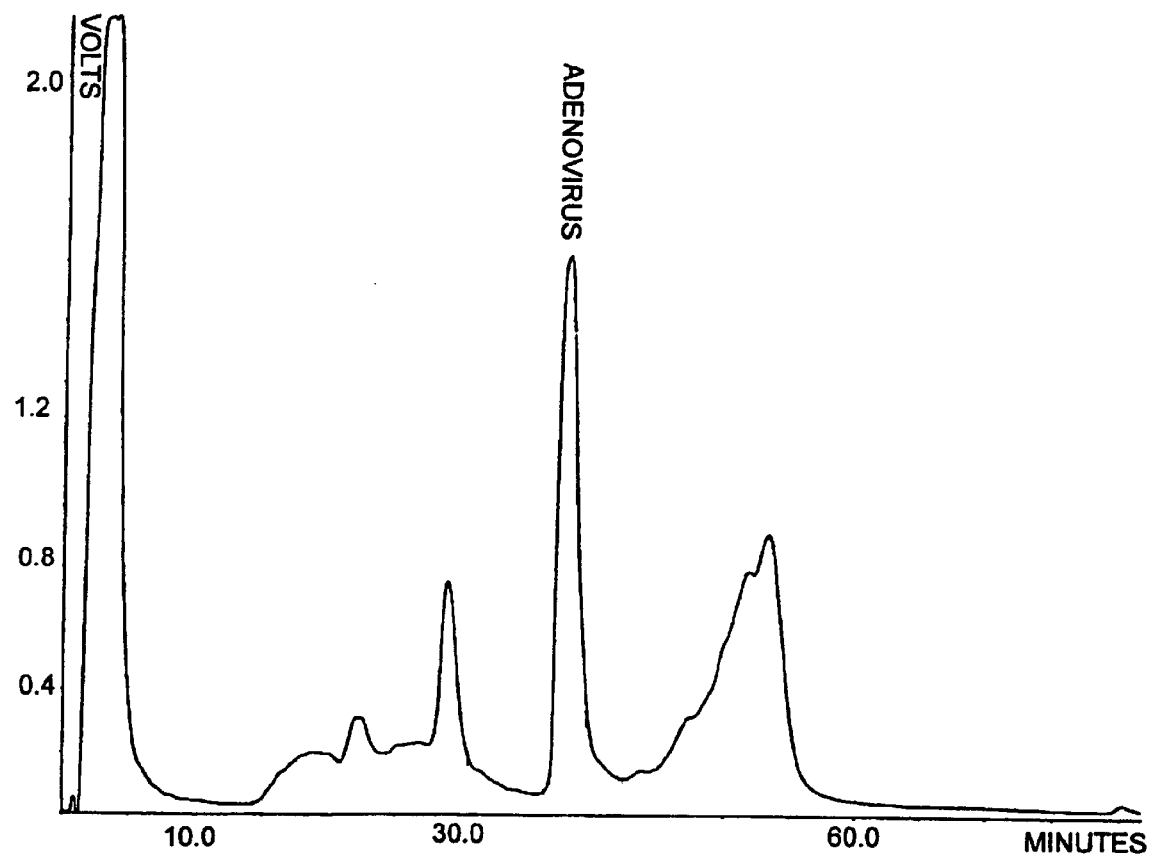

FIG. 4: Elution profile on Source Q15 of an ultrafiltered adenovirus supernatant (Example 5.1).

Figure 5:
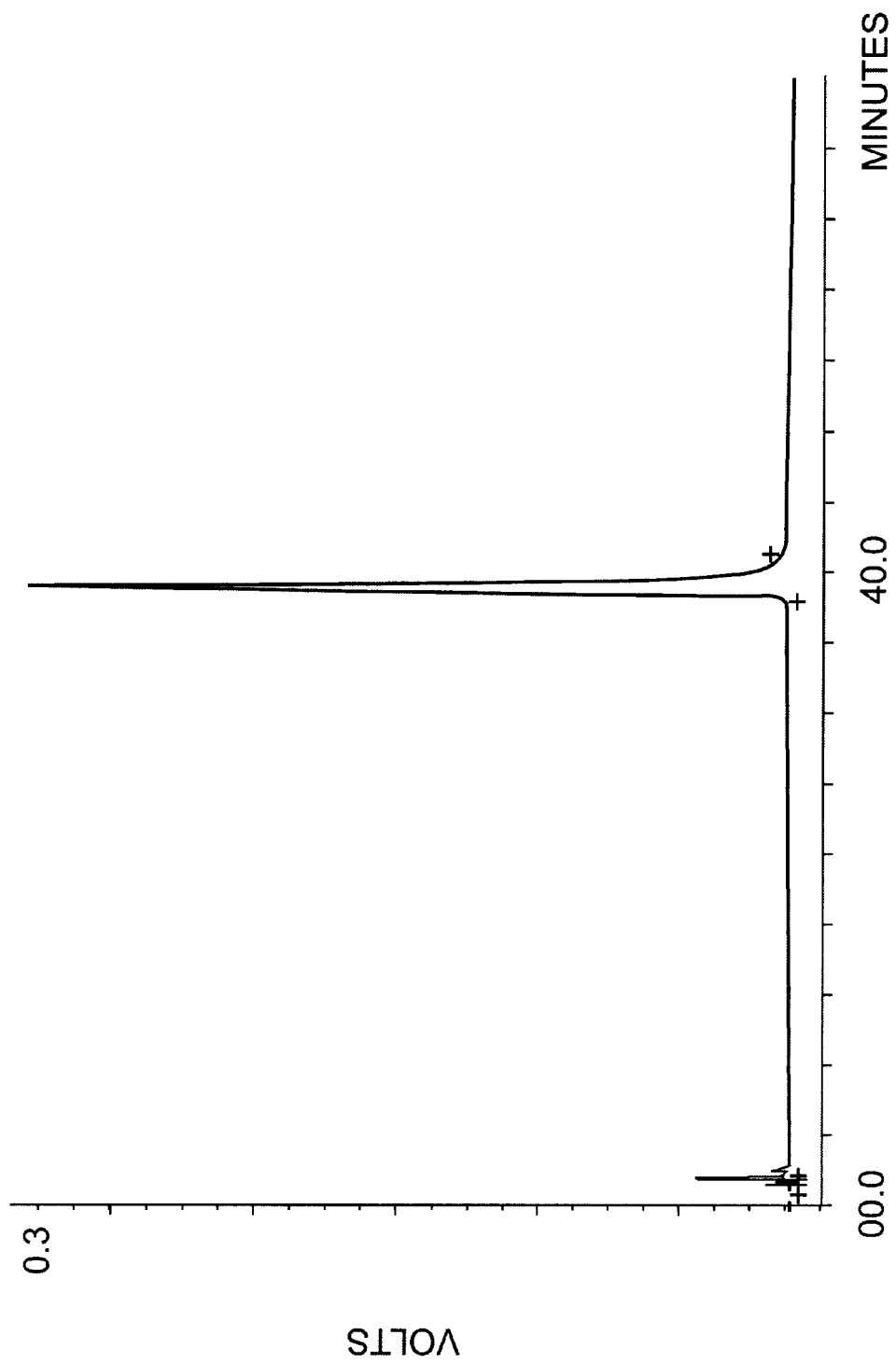

FIG. 5: Ressource Q HPLC analysis of the virus peak harvested by chromatography on a Source Q15 resin of an ultrafiltered adenovirus supernatant (Example 5.1).

Figure 6A:
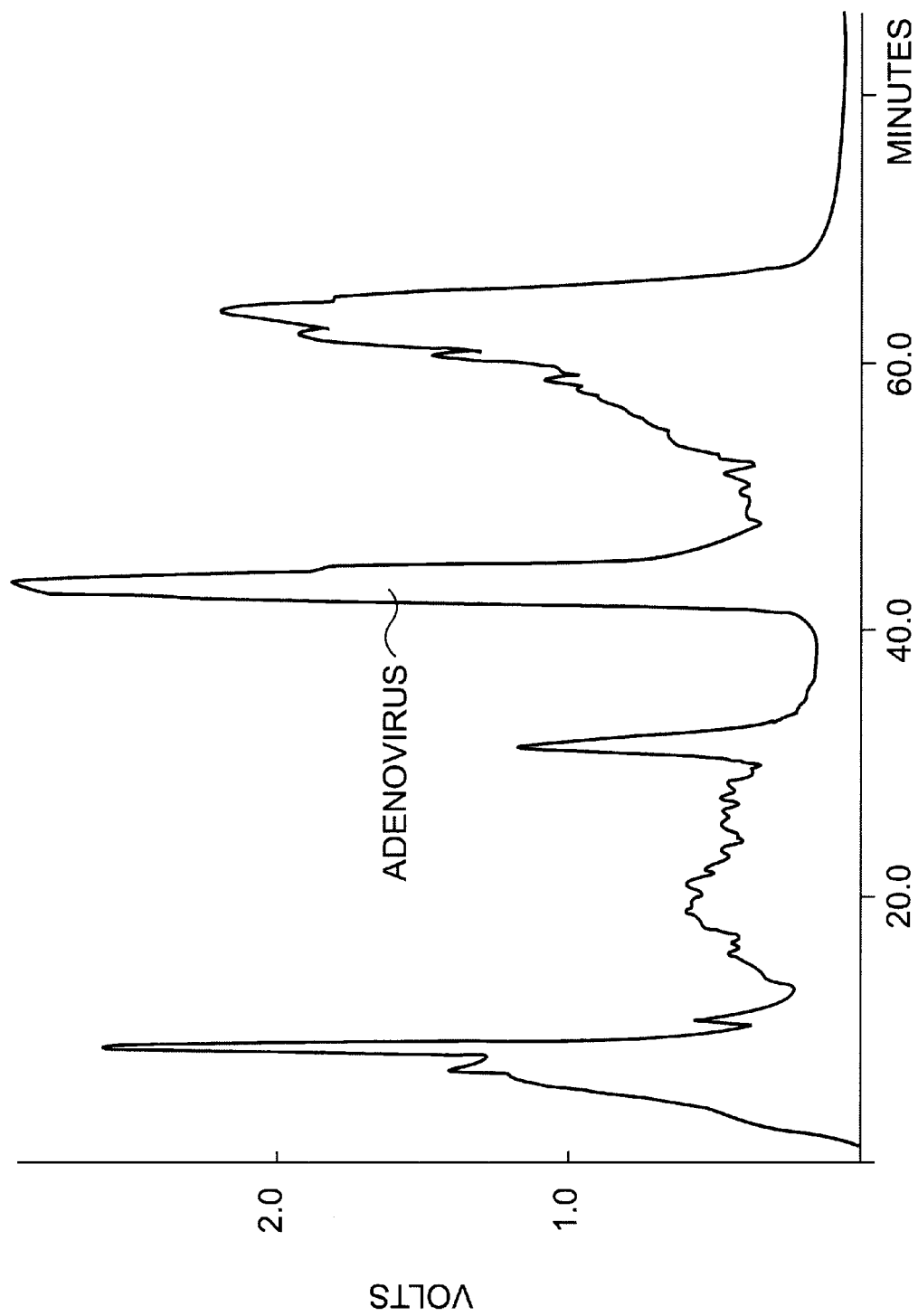

FIGS. 6A and B: (A) Elution profile on a Source Q15 resin of an ultrafiltered Ad-APOA1 adenovirus supernatant (Example 5.3); and (B) HPLC (Resource Q) analysis of the virus peak harvested.

Figure 7A:
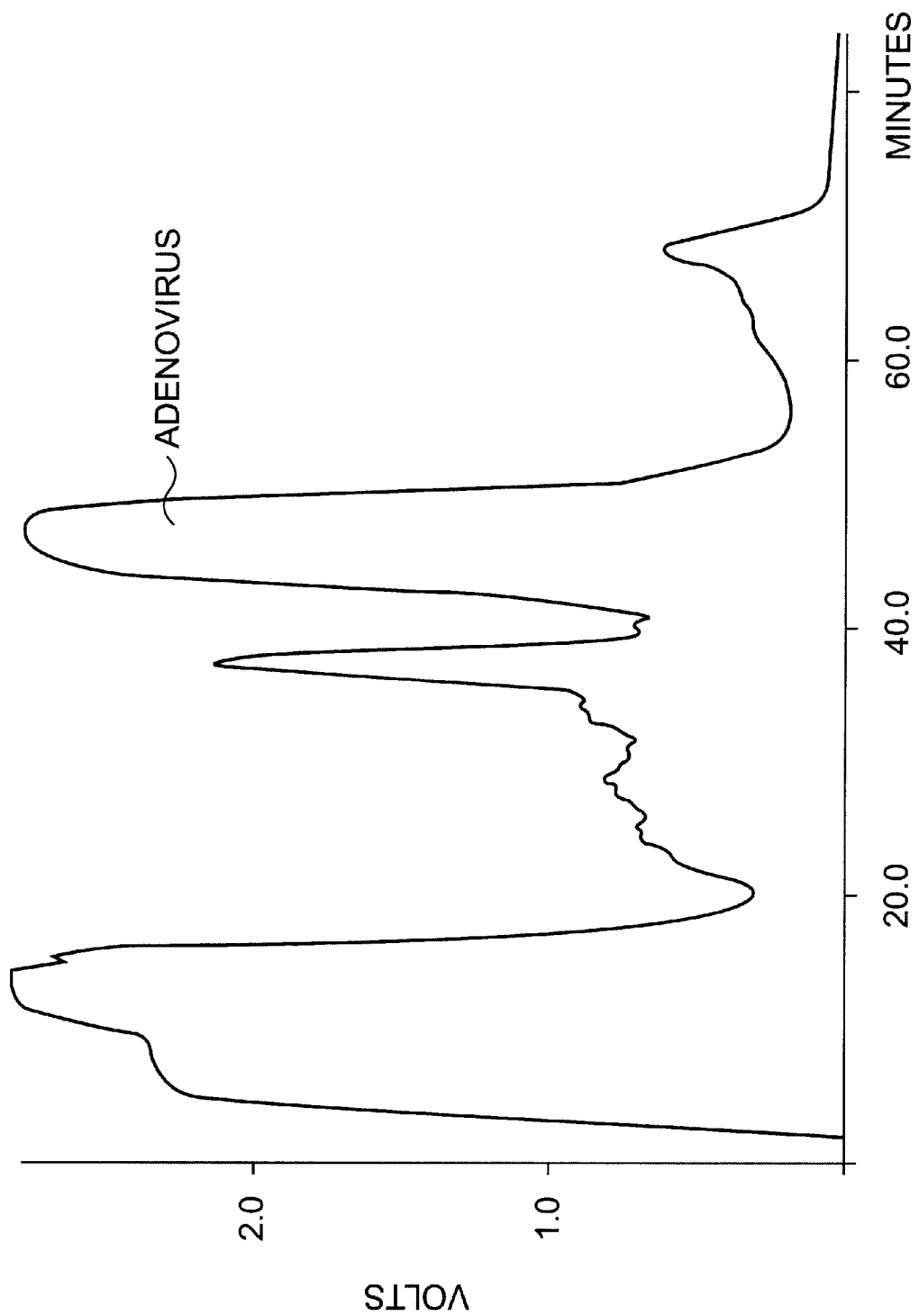

FIGS. 7A, B, C, and D: (A) Elution profile on Source Q15 of an ultrafiltered Ad-TK adenovirus supernatant (Example 5.3). HPLC (Resource Q) analysis of the various virus fractions harvested (start and end of peak): (B) Fraction F2, middle of the peak; (C) Fraction F3, limit of the peak; (D) Fraction F4, end of the peak.

Figure 8:
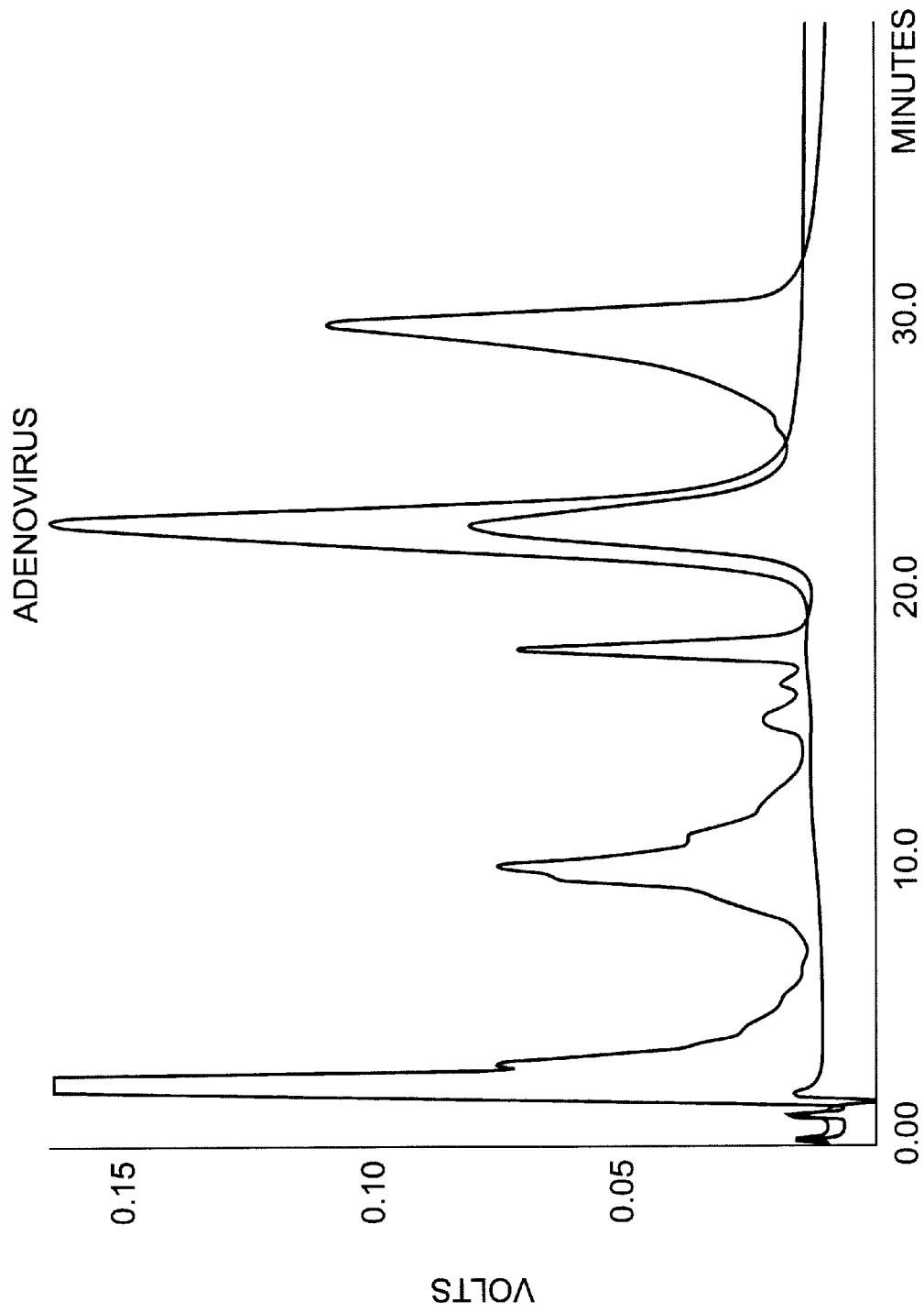

FIG. 8: Elution profile on a Mono Q resin of a concentrated supernatant of culture of adenovirus producing cells (Example 5.4). BG25F1: Supernatant virus concentrated and purified on caesium. BG25C: Concentrated infected supernatant.

Figure 9:
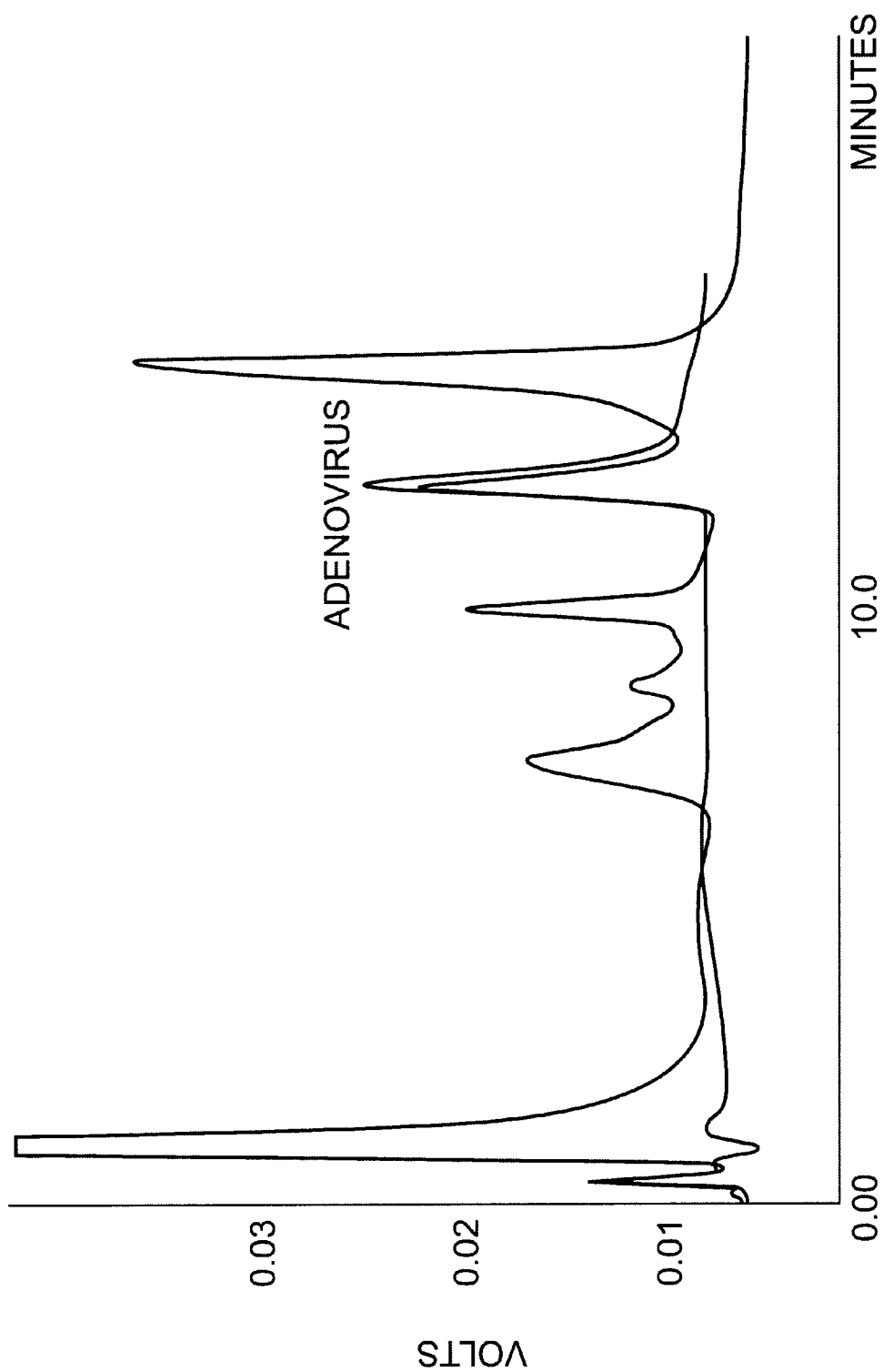

FIG. 9: Elution profile on a POROS HQ gel of a concentrated supernatant of culture of adenovirus producing cells (Example 5.4). BG25F1: Virus supernatant concentrated and purified on caesium. BG25C: Concentrated infected supernatant.

Figure 10A:
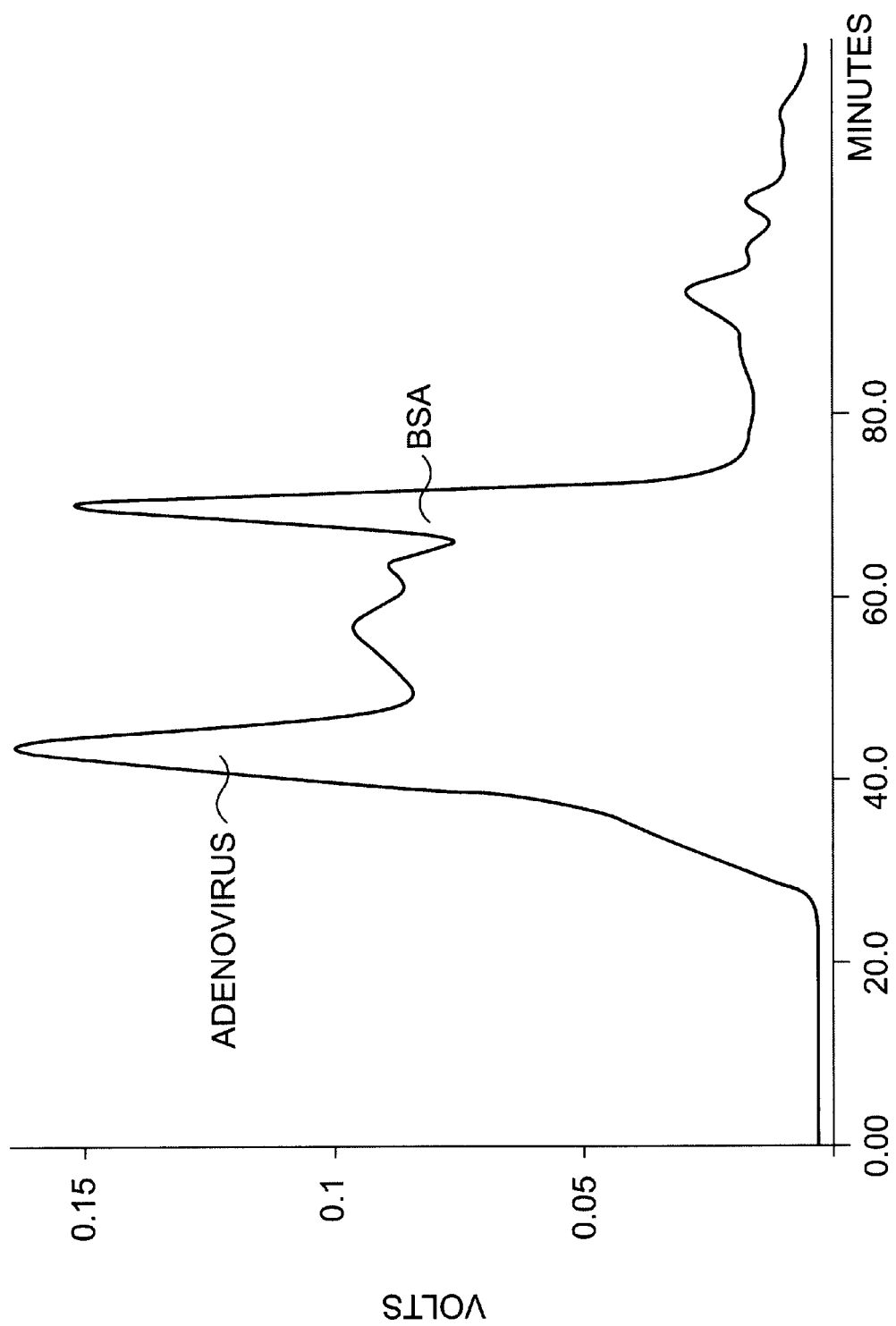
Figure 10B:
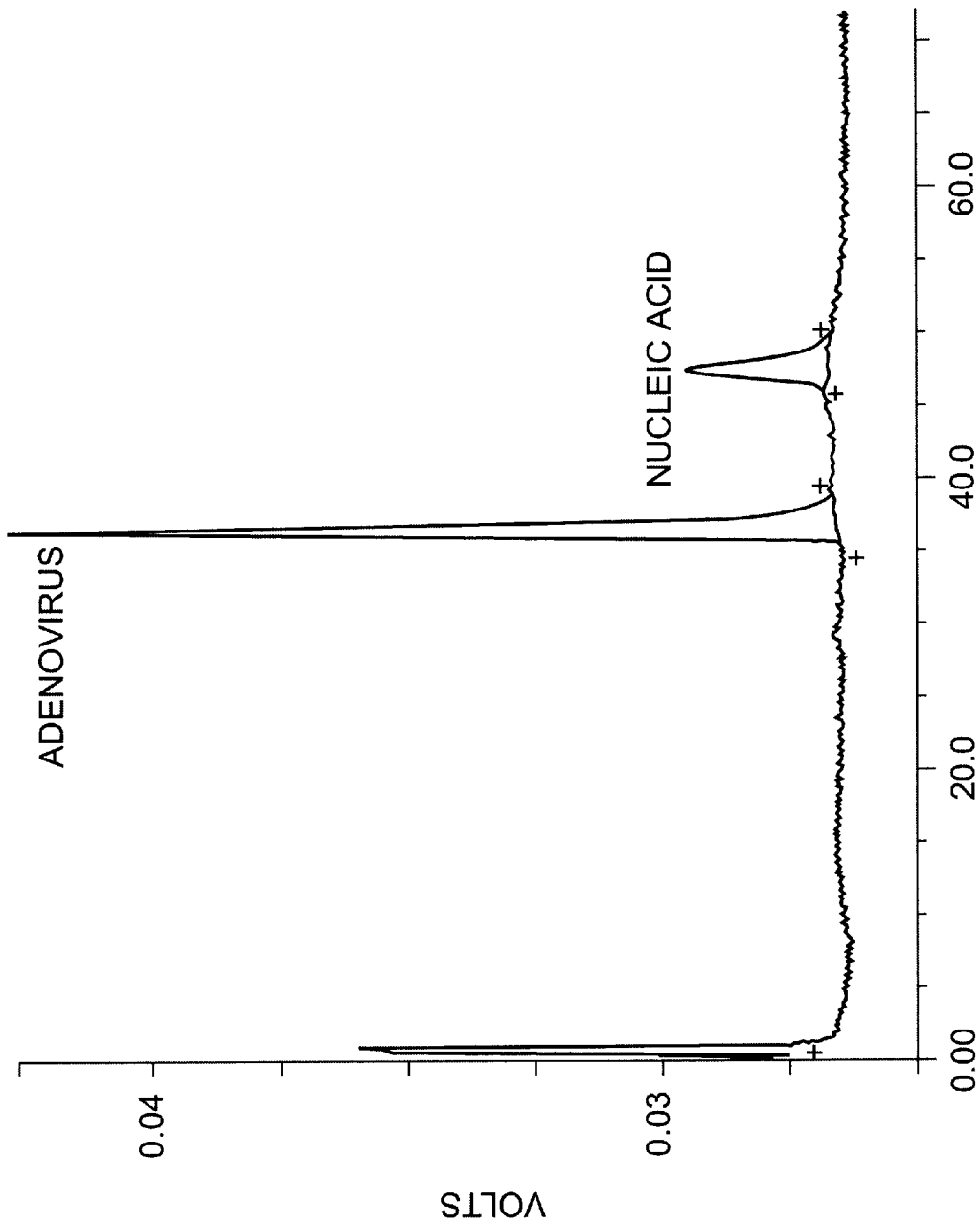

FIGS. 10 A and B: Gel permeation purification profile on Sephacryl S1000HR/Superdex 200HR of an ultrafiltered adenovirus supernatant (Example 6).

Figure 11:
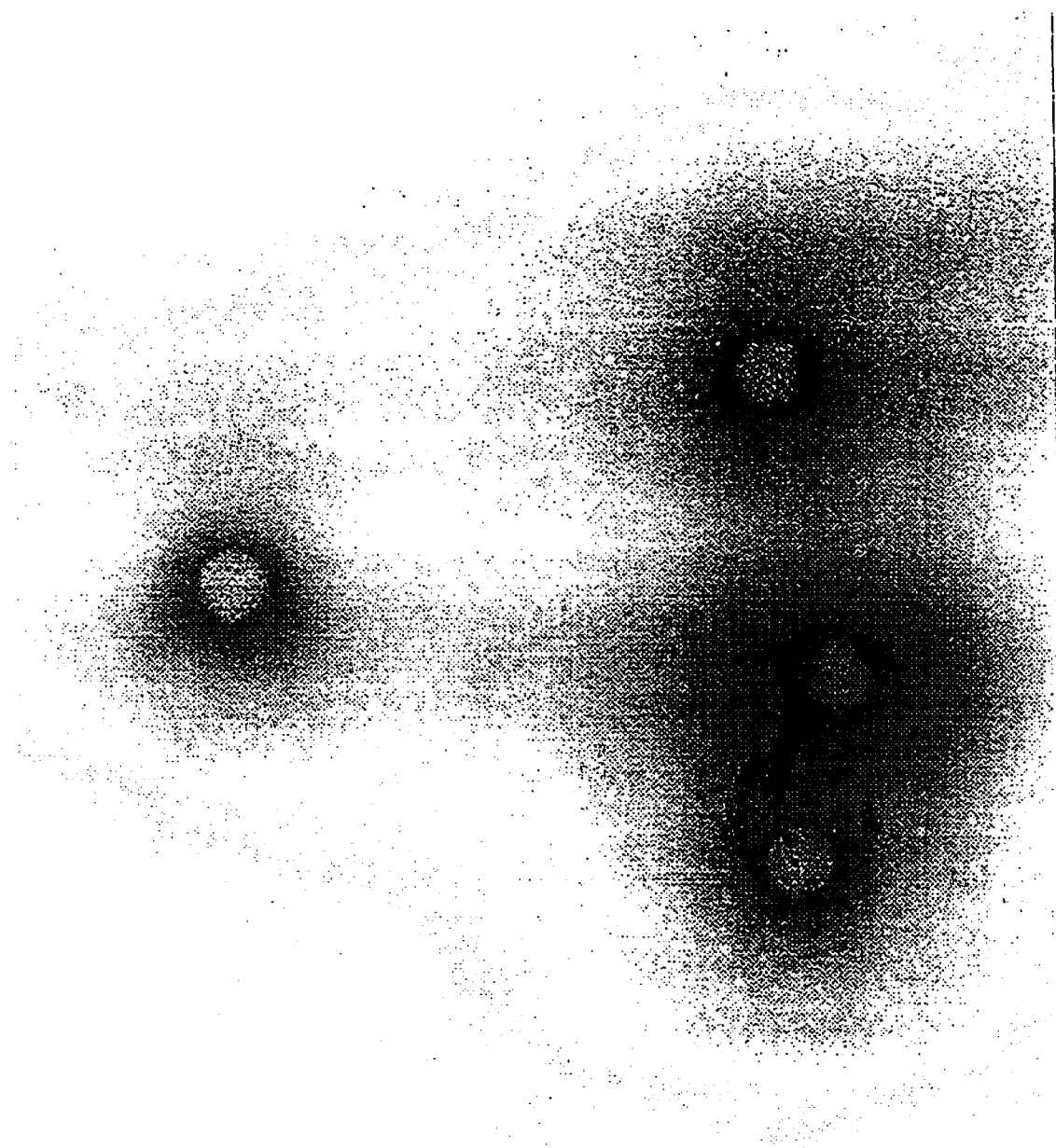

FIG. 11: Analysis by electron microscopy of a stock of adenovirus purified according to the invention.

Figure 12:
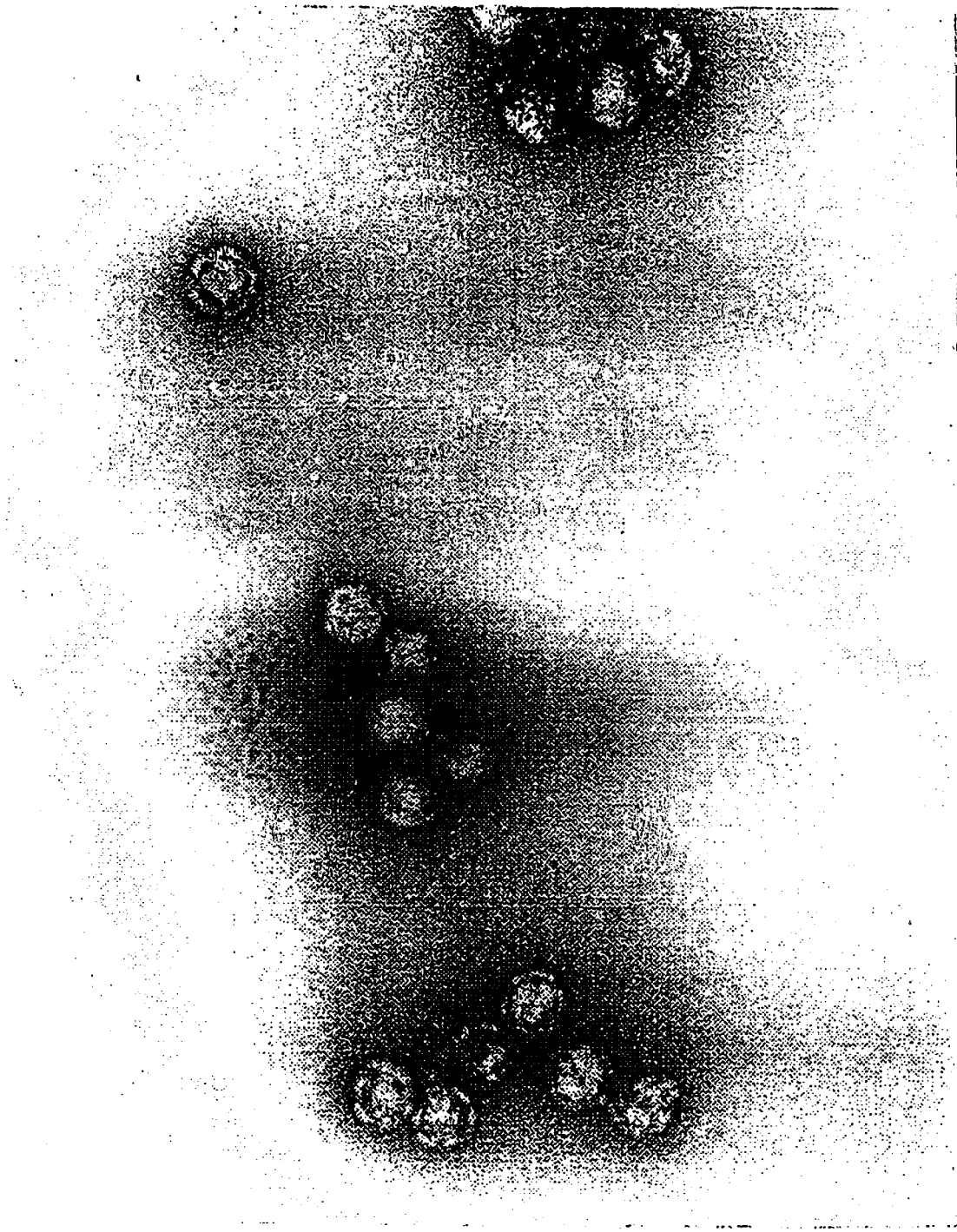

FIG. 12: Analysis by electron microscopy of the virus band of density 1.27.

GENERAL MOLECULAR BIOLOGY TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in Escherichia coli and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F.M. et al., (eds), "Current Protocols in Molecular Biology", John Wiley & Sons, New York, 19871].

The pBR322 and pUC type plasmids and the phages of the M13 series are of commercial origin (Bethesda Research Laboratories). For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier. The filling of the protruding 5' ends can be performed with the Klenow fragment of *E. coli* DNA polymerase I (Biolabs)

according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method described by Taylor et al., [Nucleic Acids Res. 13 (1985) 8749–8764] using the kit distributed by Amersham. The enzymatic amplification of the DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer. The verification of the nucleotide sequences can be performed by the method developed by Sanger et al., [Proc. Natl. Acad. Sci. USA, 74 (1977) 5463–5467] using the kit distributed by Amersham.

EXAMPLES

Example 1

Encapsidation Cell Lines

The encapsidation cells used within the framework of the invention may be obtained from any cell line which can be infected by an adenovirus and which is compatible with a use for therapeutic purposes. They are more preferably a cell chosen from the following lines:

The cells of the 293 line:

The 293 line is a human embryonic kidney cell line containing the left end (about 11–12%) of the genome of the serotype 5 adenovirus (Ad5), comprising the left ITR, the encapsidation region, the E1 region, including E1a, E1b, the region encoding the pIX protein and a portion of the region encoding the pIVa2 protein (Graham et al., J. Gen. Virol. 36 (1977) 59). This line is capable of transcomplementing recombinant adenoviruses defective for the E1 region, that is to say lacking all or part of the E1 region, and of producing viral stocks having high titres.

The cells of the A549 line

Cells complementing the adenovirus E1 region were constructed from the A549 cells (Imler et al., Gene Ther. (1996) 75). These cells contain a restricted fragment of the E1 region, lacking the left ITR, placed under the control of an inducible promoter.

The cells of the HER line

The human embryonic retinal (HER) cells may be infected with an adenovirus (Byrd et al., Oncogene 2 (1988) 477). Adenovirus encapsidation cells prepared from these cells have been described for example in Application WO 94/28152 or in the article by Fallaux et al. (Hum. Gene Ther. (1996) 215). There may be mentioned more particularly the line 911 comprising the E1 region of the Ad5 adenovirus genome, from nucleotide 79 to nucleotide 5789 integrated into the genome of HER cells. This cell line allows the production of viruses defective for the E1 region.

The IGRP2 cells

The IGRP2 cells are cells obtained from cells 293, by integration of a functional unit of the E4 region under the control of an inducible promoter. These cells allow the production of viruses defective for the E1 and E4 regions (Yeh et al., J. Virol (1996) 70).

The VK cells

The VK cells (VK2-20 and VK10-9) are cells obtained from cells 293, by integration of the entire E4 region under the control of an inducible promoter, and of the region encoding the pIX protein. These cells allow the production of viruses defective for the E1 and E4 regions (Krougliak et al., Hum. Gene Ther. 6 (1995) 1575).

The 293E4 cells

The 293E4 cells are cells obtained from cells 293, by integration of the entire E4 region. These cells allow the production of viruses defective for the E1 and E4 regions (WO 95/02697; Cancer Gene Ther. (1995) 322).

Example 2

Viruses Used

The viruses produced in the context of the examples which follow are an adenovirus containing the E. coli LacZ marker gene (Ad-βGal), an adenovirus containing the gene encoding the type I herpes virus thymidine kinase (Ad-TK), an adenovirus containing the gene encoding the human p53 tumour suppressor protein and a virus encoding the apolipoprotein A1 (Ad-apoAI). These viruses are derived from the Ad5 serotype and possess the following structure:

A deletion in the E1 region covering, for example, nucleotides 382 (HinfI site) to 3446 (Sau3a site).

A cassette for expression of the gene, under the control of the RSV or CMV promoter, inserted at the level of the said deletion.

A deletion of the E3 region.

The construction of these viruses has been described in the literature (WO 94/25073, WO 95/14102, FR 95.01632, Stratford-Perricaudet et al. J. Clin. Invest (1992) p626). It is understood that any other construct may be produced according to the process of the invention, and especially viruses carrying other heterologous genes and/or other deletions (E1/E4 or E1/E2 for example).

Example 3

Production of Virus by Lysis of the Cells

This example reproduces the previous technique for producing viruses, consisting in lysing the encapsidation cells in order to recover the viruses produced.

The cells 293 are infected at 80–90% confluence in a culture dish with a prestock of Ad-βGal or Ad-TK virus (Example 2) in an amount of 3 to 5 viruses per cell (Multiplicity of Infection MOI =3 to 5). The incubation lasts for 40 to 72 hours, the timing of the harvest being determined by observing, under a microscope, cells which become round, become more refringent and adhere increasingly weakly to the culture support. In the literature, the kinetics of the viral cycle lasts for 24 to 36 hours.

At the level of the laboratory production, it is important to harvest the cells before they become detached so as to remove the infection medium at the time of the harvest without losing cells and then to take them up in a minimum volume (the concentration factor is, depending on the size of the culture, of the order of 10 to 100 fold).

The virus is then released from the nucleus by 3 to 6 successive thawing cycles (ethanol-dry ice at −70° C., water bath at 37° C.).

The cell lysate obtained is then centrifuged at low speed (2000 to 4000 rpm) and the supernatant (clarified cell lysate)

is then purified by ultracentrifugation on a caesium chloride gradient in two steps:

A first rapid ultracentrifugation (step) of 1.5 hours, 35000 rpm, rotor sw 41, on two caesium layers 1.25 and 1.40 flanking the virus density (1.34) so as to separate the virus from the proteins in the medium; the rotors may be "swinging" rotors (Sw28, Sw41 Beckman) or fixed angle rotors (Ti 45, Ti 70, Ti 70.1 Beckman) depending on the volumes to be treated;

A second, longer gradient ultracentrifugation (from 10 to 40 hours depending on the rotor used), for example 18 hours at 35000 rpm in sw 41 rotor which constitutes the actual and sole virus purification. The virus is present in a linear gradient at equilibrium at a density of 1.34.

Generally, at this stage, the virus band is predominant. Nevertheless, two fine, less dense bands are sometimes observed whose examination by electron microscopy has shown that they are empty or broken viruses and for the least dense band, viral subunits (pentons, hexons). After this step, the virus is harvested in the tube by piercing with a needle and the caesium is removed by dialysis or desalting on G25.

Example 4

Production of Virus in the Supernatant

This example describes an experiment for the production of virus by recovering following spontaneous release. The virus is then harvested by ultrafiltration and then purified by caesium chloride.

4.1. Procedure

In this method, unlike Example 3, the cells are not harvested 40 to 72 hours post-infection, but the incubation is extended between 8 to 12 days so as to obtain total lysis of the cells without the need to carry out the freeze-thaw cycles. The virus is present in the supernatant.

The supernatant is then clarified by filtration on depth filters of decreasing porosity (10 $\mu$m/1.0 $\mu$m/0.8-0.2 $\mu$m).

The virus has a size of 0.1 $\mu$m and at this stage, no loss of virus by retention on the filter at the lowest porosity (0.22 $\mu$m) was observed.

The supernatant, once clarified, is then concentrated by tangential ultrafiltration on a Millipore spiral membrane having a cut-off of 300 kDa.

In the experiments reported in the present invention, the concentration factor is dictated by the dead volume of the system which is 100 ml. Supernatant volumes of 4 to 20 liters were concentrated with this system, making it possible to obtain concentrate volumes of 100 ml to 200 ml without difficulty, which corresponds to a concentration factor of 20 to 100 fold.

The concentrate is then filtered on 0.22 $\mu$m and then purified by centrifugation on caesium chloride as described in Example 3, followed by a dialysis step.

4.2 Results

Purity

Whereas the intracellular virus tube (Example 3) has a cloudy appearance with a coagulum (lipids, proteins) which sometimes touches the virus band, the viral preparation obtained after the first centrifugation step on caesium chloride by the process of the invention has a virus band which is already well isolated from the contaminants in the medium which persist in the top phase. High-performance liquid chromatography analysis on a Resource Q column (cf Example 5) also shows this gain in the purity of the starting material obtained by ultrafiltration of infected supernatant with a decrease in the nucleic acid contaminants (OD 260/280 ratio greater than or equal to 1.8) and protein contaminants (OD 260/280 ratio less than 1).

Stability of the Virus in a Supernatant at 37° C.

The stability of the virus was determined by titration, by the plaque assay method, of an infectious culture supernatant of which aliquots were collected at various incubation times at 37° C. post-infection. The results are presented below:

Ad-TK virus:
titre 10 days post-infection=3.5×10$^8$ pfu/ml
titre 20 days post-infection=3.3×10$^8$ pfu/ml Ad-βGal virus
titre 8 days post-infection=5.8×10$^8$ pfu/ml
titre 9 days post-infection=3.6×10$^8$ pfu/ml
titre 10 days post-infection=3.5×10$^8$ pfu/ml
titre 13 days post-infection=4.1×10$^8$ pfu/ml
titre 16 days post-infection=5.5×10$^8$ pfu/ml The results obtained show that up to at least 20 days post-infection, the titre of the supernatant is stable within the limits of precision of the assay. Moreover, FIG. 1 shows that, in the elution buffer, the virus is stable for at least 8 months, at −80° C. and at −20° C.

Specific Infectivity of the Preparations

This parameter, corresponding to the ratio of the number of viral particles measured by HPLC to the number of pfu, gives information on the infectivity of the viral preparations. According to the recommendations of the FDA, it should be less than 100. This parameter was measured as follows: Two series of culture flasks containing cells 293 were infected in parallel at the same time with the same viral prestock under the same conditions. This experiment was carried out for a recombinant Ad-βgal adenovirus, and then repeated for an Ad-TK adenovirus. For each adenovirus, a series of flasks is harvested 48 hours post-infection and is considered as a production of intracellular virus purified on a caesium gradient after freezing-thawing. The other series is incubated for 10 days post-infection and the virus is harvested in the supernatant. The purified preparations obtained are titrated by plaque assay and the quantification of the total number of viral particles is determined by measuring the concentration of PVII protein by reversed phase HPLC on a C4 Vydac 4.6×50 mm column after denaturation of the samples in 6.4 M guanidine. The quantity of PVII proteins is correlated to the number of viral particles considering 720 copies of PVII per virus (Horwitz, Virology, second edition (1990)). This method is correlated with the measurements of viral particles on preparations purified by the densitometric method at 260 nm, taking as specific extinction coefficient 1.0 unit of absorbance =1.1×10$^{12}$ particles per ml.

The results obtained show that, for the Ad-βGal virus, this ratio is 16 for the supernatant virus and 45 for the intracellular virus. For the Ad-TK virus, the ratio is 78 in the case of the virus harvest in the supernatant method and 80 for the virus harvested by the intracellular method.

Analysis by Electron Microscopy

This method makes it possible to detect the presence of empty particles or free viral subunits copurified, and to assess a protein contamination of the purified viral preparations or the presence of non-dissociable aggregates of viral particles.

Procedure: 20 $\mu$l of sample are deposited on a carbon grid and then treated for the examination by negative staining with 1.5% uranyl acetate. For the examination, a 50 kV to 100 kV Jeol 1010 electron microscope is used.

Result: The analysis carried out on a virus harvested in the supernatant shows a clean preparation, without contaminants, without aggregates and without empty viral particles. It is furthermore possible to distinguish the virus fibres as well as its regular geometric structure. These results confirm the high quality of the viral particles obtained according to the invention.

HPLC and SDS-PAGE Analysis of the Protein Profile

SDS-PAGE Analysis

20 μl of sample is diluted in Laemmli buffer (Nature 227 (1970) 680–685), reduced for 5 min at 95° C., and then loaded onto Novex gels 1 mm×10 wells gradient 4–20%. After migration, the gels are stained with coomassie blue, and analysed on a Pharmacia VDS Image Master. The analysis reveals an electrophoretic profile for the virus harvested in the supernatant in agreement with the literature data (Lennart Philipson, 1984 H. S. Ginsberg editors, Plenum press, 310–338).

Reversed phase HPLC analysis

FIG. 2 shows the superposition of 3 chromatograms obtained from two virus samples harvested intracellularly and a virus sample purified by the supernatant method. The experimental conditions are the following: Vydac column ref. 254 Tp 5405, RPC4 4.6×50 mm, Solvent\A: H20+TFA 0.07%; Solvent B:CH3CN+TFA 0.07%, linear gradient: T=0 min %B=25; T-50 min %B=50%; flow rate=1 ml/min, detector=215 nm. The chromatograms show a perfect identity between the samples, without difference in the relative intensities of each peak. The nature of each peak was determined by sequencing and shows that the proteins present are all of viral origin (see table below).

| PEAK (Min) | IDENTIFICATION |
|---|---|
| 19–20 | Precursor PVII |
| 21–22 | Precursor PVII; Precursor PX 1 to 12 |
| 27–28 | Precursor PVI; Precursor PX |
| 32–33 | Precursor PX |
| 34 | |
| 35–36 | Mature PVII |
| 37 | Mature PVII; PVIII precursor |
| 39–41 | Mature PVI |
| 45 | pX |
| 46 | pIX |

Analysis in Vitro of the Efficiency of Transduction and of the Cytotoxicity

The analysis of the cytotoxicity is carried out by infecting HCT116 cells in 24-well plates for increasing MOIs and by determining the percentage of live cells compared with a non-infected control, 2 and 5 days post-infection, with the aid of the crystal violet staining technique.

The results are presented in the table below:

| Adenovirus | MOI = 3.0 | MOI = 10.0 | MOI = 30.0 | MOI = 100.0 |
|---|---|---|---|---|
| Supernatant, D2 | 91% | 96% | 87% | 89% |
| Supernatant, D5 | 97% | 90% | 10% | <5% |

Analysis of the transduction efficiency

For an AD-βGal adenovirus, the transduction efficiency of a preparation is determined by infecting W162 cells, non-permissive to replication, cultured in 24-well plates, with increasing concentrations of viral particles. For the same quantity of viral particles deposited, the cells expressing the beta-galactosidase activity are counted 48 hours post-infection after incubation with X-gal as substrate. Each blue cell is counted as one transduction unit (TDU), the result is multiplied by the dilution of the sample so as to obtain the concentration in units of transduction of the sample. The transduction efficiency is then expressed by calculating the ratio of the concentration of viral particles to the concentration in TDU. The results obtained show that the purified viruses have a good transduction efficiency in vitro.

Analysis of the Intracerebral Expression in Vivo

With the aim of evaluating the efficiency of the adenoviruses according to the invention for the transfer and expression of genes in vivo, the adenoviruses were injected by the stereotaxic route into the striatum of OF1 immunocompetent mice. For that, volumes of 1 μl at $10^7$ pfu of virus were injected at the following stereotaxic reference points (for the incision line at 0 mm): anteroposterior: +0.5; mediolateral: 2; depth: −3.5.

The brains were analysed 7 days after the injection. The results obtained show that the transduction efficiency is high: thousands of transduced cells, very intense expression in the nucleus and frequent and intense diffusion in the cytoplasm.

4.3. Kinetics of Release of the Virus

This example describes a study of the kinetics of release of adenoviruses in the encapsidation cell culture supernatant.

This study was carried out by semiquantitative PCR by means of oligonucleotides complementary to the regions of the adenovirus genome. To this effect, the linearized viral DNA (1–10 ng) was incubated in the presence of dXTP (2 μl, 10 mM), a pair of specific oligonucleotides and Taq polymerase (Cetus) in a 10X PCR buffer, and subjected to 30 amplification cycles under the following conditions: 2 min at 91° C., 30 cycles (1 min 91° C., 2 min at annealing temperature, 3 min at 72° C.), 5 min 72° C., then 4° C. PCR experiments were carried out with the pairs of oligonucleotides of sequence:

```
Pair 1:
TAATTACCTGGGCGGCGAGCACGAT  (6368) - SEQ ID No. 1

ACCTTGGATGGGACCGCTGGGAACA  (6369) - SEQ ID No. 2

Pair 2:
TTTTTGATGCGTTTCTTACCTCTGG  (6362) - SEQ ID No. 3

CAGACAGCGATGCGGAAGAGAGTGA  (6363) - SEQ ID No. 4

Pair 3:
TGTTCCCAGCGGTCCCATCCAAGGT  (6364) - SEQ ID No. 5

AAGGACAAGCAGCCGAAGTAGAAGA  (6365) - SEQ ID No. 6

Pair 4:
GGATGATATGGTTGGACGCTGGAAG  (6366) - SEQ ID No. 7

AGGGCGGATGCGACGACACTGACTT  (6367) - SEQ ID No. 8
```

The quantity of free adenovirus in the supernatant was determined on a supernatant of cells 293 infected with Ad-βGal, at various times post-infection. The results obtained are presented in FIG. 3. They show that the cellular release starts from the 5th or 6th day post-infection.

It is understood that any other virus determination technique may be used with the same objective, on any other encapsidation line, and for any adenovirus type.

Example 5

Purification of the Virus by Ultrafiltration and Ion Exchange

This example illustrates how the adenovirus contained in the concentrate may be purified directly and in a single ion-exchange chromatography step, with very high yields.

5.1. Procedure

In this experiment, the starting material therefore consists of the concentrate (or ultrafiltration retentate) described in Example 4. This retentate has a total protein content of between 5 and 50 mg/ml, and more preferably between 10 and 30 mg/ml, in PBS buffer (10 mM phosphate, pH 7.2 containing 150 mM NaCl).

The ultrafiltration supernatant obtained from a virus preparation is injected into a column containing Source Q 15 (Pharmacia) equilibrated in 50 mM Tris-HCl buffer pH 8.0 containing 250 mM NaCl, 1.0 mM $MgCl_2$ and 10% glycerol (buffer A). After rinsing with 10 column volumes of buffer A, the adsorbed species are eluted with a linear NaCl gradient (250 mM to 1 M) on 25 column volumes at a linear flow rate of 60 to 300 cm/h, more preferably 12 cm/h. The typical elution profile obtained at 260 nm is presented in FIG. 4. The fraction containing the viral particles is collected. It corresponds to a fine symmetrical peak whose retention time coincides with the retention time obtained with a preparation of viral particles purified by ultracentrifugation. It is possible to inject, under the conditions described above, a minimum of 30 mg of total proteins per ml of Source Q 15 resin while preserving an excellent resolution of the viral particle peak.

In a representative experiment carried out using a β-gal adenovirus preparation (Example 2), 12.6 mg of total proteins were injected onto a Resource Q column (1 ml), that is to say $5 \times 10^{10}$ PFU and $1.6 \times 10^{10}$ TDU. The viral particle peak collected after chromatography (3.2 ml; FIG. 5) contained 173 μg of proteins and $3.2 \times 10^{10}$ PFU and $2.3 \times 10^{10}$ TDU. The viral particles were therefore purified 70 fold (in terms of quantity of proteins) and the purification yield is 64% in PFU and 142% in TDU (see table below).

to 1 M) in the B buffer at a flow rate of 1 ml/min. The eluted species are detected at 260 nm. This HPLC analysis (FIG. 5) shows, furthermore, that the residual bovine serum albumin present in the ultrafiltration retentate is completely removed during the preparative chromatography. Its content in the purified fraction is estimated to be <0.1%. Western blot analysis with an anti-BSA polyclonal antibody (with ECL revealing; Amersham) indicates that the content of BSA in the chromatographic preparation is less than 100 ng per mg of virus.

The electrophoretic analysis of the adenoviral fraction purified by chromatography is performed on a polyacrylamide gel (4–20%) under denaturing (SDS) conditions. The protein bands are then revealed with silver nitrate. This analysis shows that the adenoviral preparation obtained by chromatography has a purity level at least equal to that of the preparation conventionally obtained by ultracentrifugation since it has no additional protein band which would indicate a contamination of the preparation by non-adenoviral proteins.

The adenoviral preparation obtained by chromatography has an absorbance ratio $A_{260\ nm}/A_{280\ nm}$ equal to 1.30±0.05. This value, which is identical to that obtained for the best preparations obtained by ultracentrifugation, indicates that the preparation is free of contaminating proteins or of contaminating nucleic acids.

Analysis by electron microscopy carried out under the conditions described in Example 4.2 on a chromatography-purified Ad-βgal virus shows a clean preparation, without contaminants, without aggregates and without empty viral particles (FIG. 11). Furthermore, caesium chloride gradient ultracentrifugation of this preparation reveals a single band of density 1.30, which confirms the absence of contamina-

| Steps | Concentration sample | Volumes deposited | Volumes recovered | Yields | Purification factor |
|---|---|---|---|---|---|
| SUPERNATANT | | 5000 ml | 5000 ml | 100% | — |
| ULTRA-FILTRATION 300 kd | Proteins: 6.3 mg/ml<br>PFU: $2.5 \times 10^{10}$/ml<br>TDU: $8.1 \times 10^9$/ml<br>Particle $3.8 \times 10^{11}$/ml<br>Part/pfu ratio: 16.0<br>Part/tdu ratio: 47.0 | 5000 ml | 200 ml | 100% | 5 |
| ION-EXCHANGE PURIFICATION (one step) | PFU: $1.0 \times 10^{10}$/ml<br>TDU: $7.2 \times 10^9$/ml<br>Particle: $2.0 \times 10^{11}$/ml<br>Part/pfu ratio = 20<br>Part/tdu ratio = 27 | 2.0 ml of concentrate | 3.0 ml of elution | Proteins = 85%<br>PFU = 64%<br>TDU = 140%<br>Particles = 84%<br>HPLC<br>Purity = 98.4% | 70 |
| CsCl GRADIENT | PFU: $1.0 \times 10^{11}$/ml<br>TDU: $7.5 \times 10^{10}$/ml<br>Particle: $2.2 \times 10^{12}$/ml<br>Part/pfu ratio = 22<br>Part/tdu ratio = 29 | 28.3 ml of concentrate | QSP 4.1 ml | PFU = 66%<br>TDU = 130%<br>Particles = 84%<br>HPLC<br>purity = 98.4% | 70 |

5.2. Purity

After this purification step, the fraction collected has a purity ≧98% of viral particles (UV detection at 260 nm), when it is analysed by high-performance liquid chromatography (HPLC) on a Resource Q column (1 ml) in the following chromatographic system: (10 μl of fraction purified by chromatography as described in Example 5.1 are injected into a Resource Q15 column (1 ml of gel; Pharmacia) equilibrated in 50 mM Tris/HCl buffer pH 8.0 (buffer B). After rinsing with 5 ml of buffer B, the adsorbed species are eluted with a linear gradient of 30 ml of NaCl (0 tion of the chromatographic preparations by potential empty particles or capsid fragments. During the purification, the chromatographic peak for the virus is followed by a shoulder (or secondary peak) in its rear portion, which is not collected with the main peak. Caesium chloride gradient ultracentrifugation of this fraction reveals a band of density 1.27, and analysis of the composition of this fraction shows that it does not contain nucleic acids. Analysis by electron microscopy shows that this fraction contains particles of irregular shape, exhibiting perforations at the surface (FIG. 12). They are therefore empty (lacking DNA) and incomplete particles.

This therefore demonstrates that the purification of the adenovirus by chromatography eliminates the empty particles present in a small quantity in the preparations before purification.

5.3. Purification of Adenoviruses Comprising a Therapeutic Gene such as the Genes Encoding the ApoA1 or Thymidine Kinase Proteins.

This example illustrates how adenoviruses comprising, in their genomes, heterologous nucleic acid sequences encoding therapeutic proteins may be purified directly and in a single ion-exchange chromatography step. It also shows that the chromatographic behaviour of the adenovirus is identical to the heterologous nucleic acid sequences which it carries, allowing the same purification process to be used for different adenoviruses carrying various heterologous nucleic acid sequences.

Figure 6B:
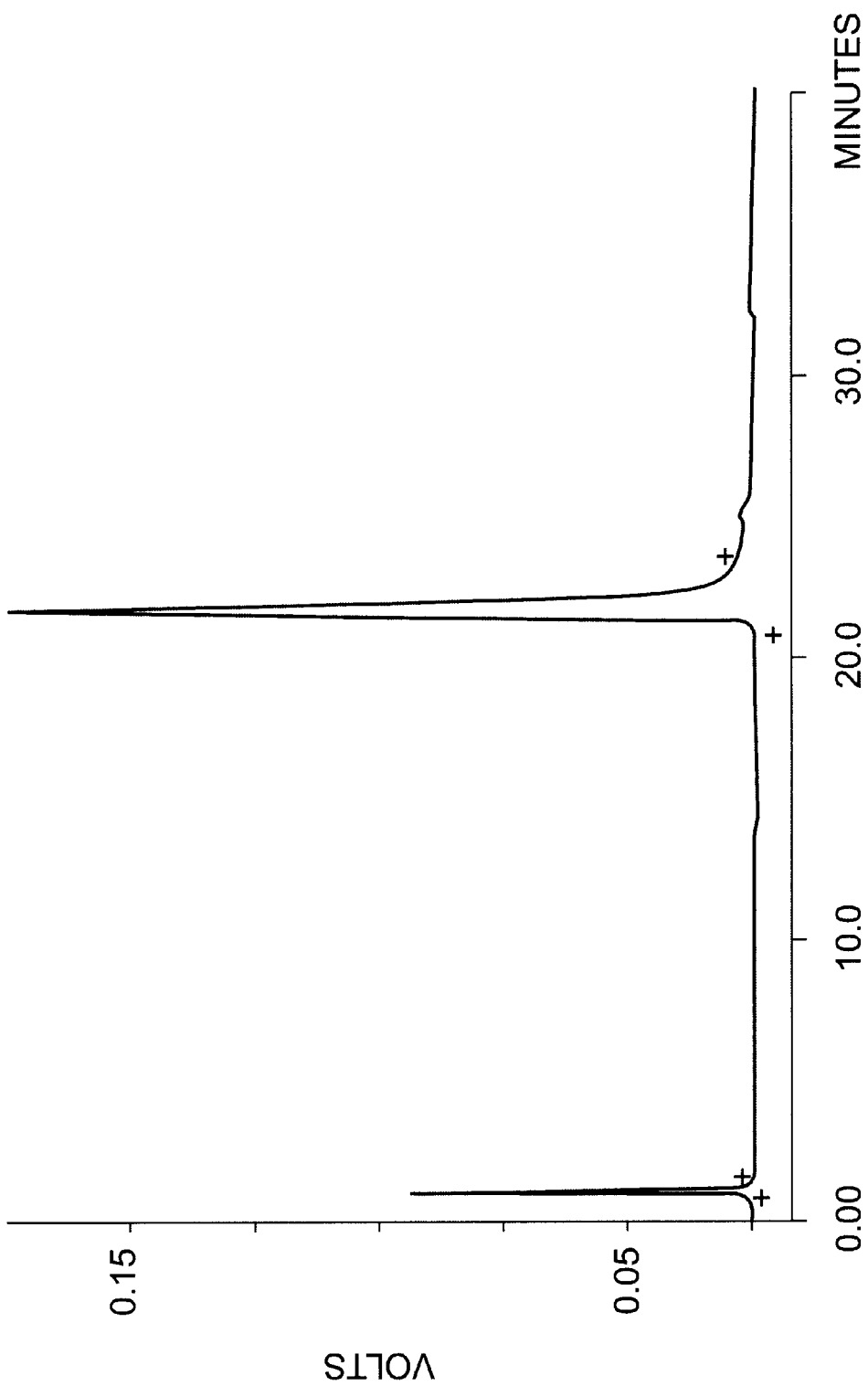

In a typical purification experiment, an adenovirus comprising, in its genome, a heterologous nucleic acid sequence encoding the ApoA1 protein (Example 2, WO 94/25073) is purified by chromatographing, in the system described in Example 5.1, 18 ml (72 mg of proteins; $1.08 \times 10^{13}$ particles) of concentrated supernatant of a cell culture harvested 10 days post-infection (FIG. 6A). The viral particle peak collected after chromatography (14 ml; 1.4 mg of proteins) contained $9.98 \times 10^{12}$ particles, which indicates a particle yield of 92% and a purification factor of 51. After this purification step, the fraction collected had (FIG. 6B) a purity greater than 98% as viral particles during the chromatographic analysis under the conditions described in 5.2. The electrophoretic analysis of the adenoviral fraction purified by chromatography carried out under the conditions described in Example 5.2 showed that this preparation had a purity level at least equal to that for the preparation conventionally obtained by ultracentrifugation, and that it is free of contaminating proteins or of contaminating nucleic acids.

Figure 7B:
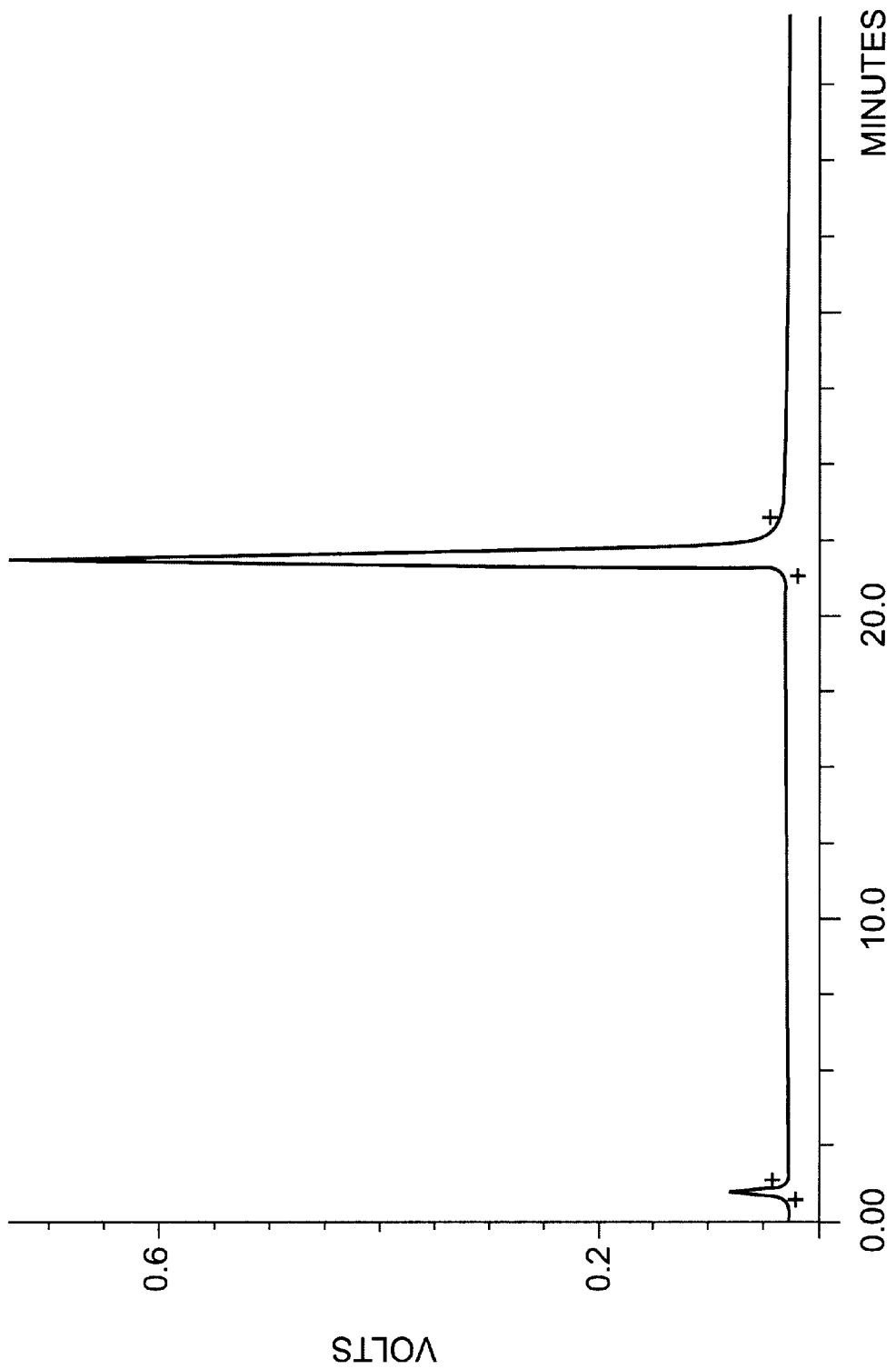
Figure 7C:
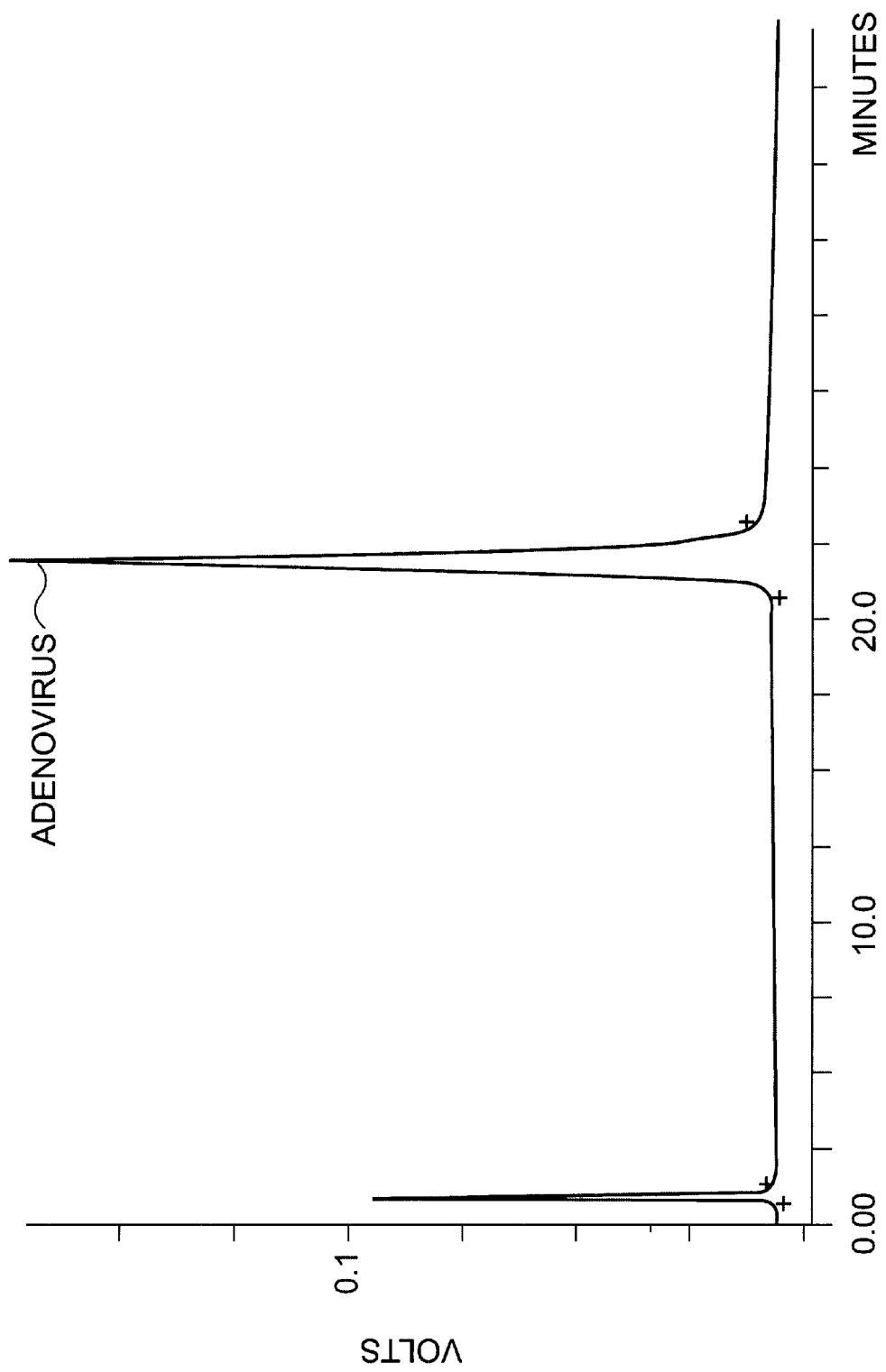
Figure 7D:
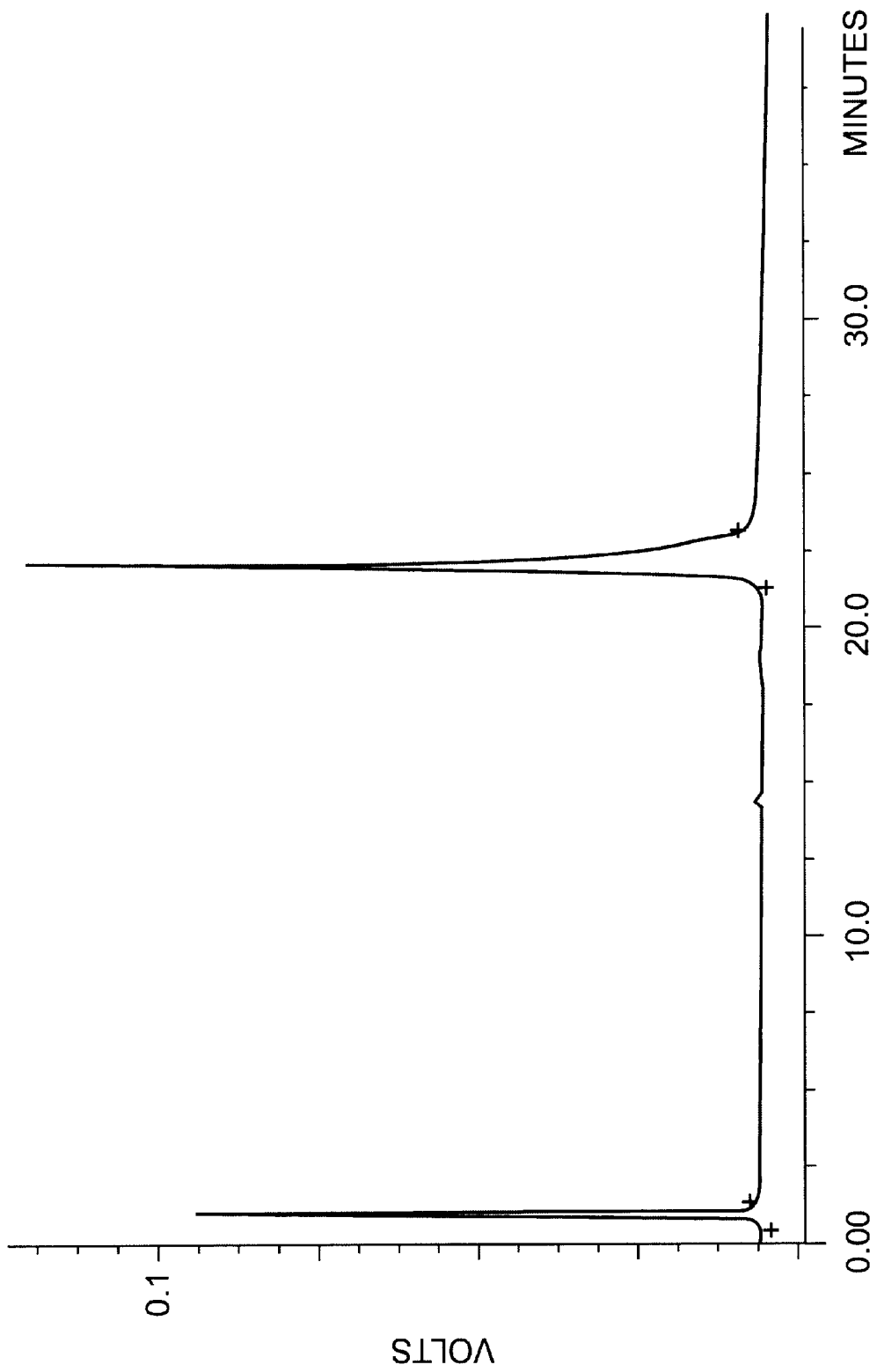

In another typical purification experiment, an adenovirus comprising, in its genome, a heterologous nucleic acid sequence encoding the type 1 herpes simplex thymidine kinase protein (Example 2, WO 95/14102) is purified by chromatographing, in the system described in Example 5.1, 36 ml (180 mg of proteins; $4.69 \times 10^{13}$ particles) of concentrated supernatant of a cell culture (FIG. 7A). The viral particle peak collected after chromatography (20 ml; 5.6 mg of proteins) contained $4.28 \times 10^{13}$ particles, which indicates a particle yield of 91% and a purification factor of 32. After this purification step, the fraction collected had (FIGS. 7B–D) a purity greater than 99% as viral particles during the chromatographic analysis under the conditions described in Example 5.2 and an absorbance ratio of 1.29. The electrophoretic analysis of the adenoviral fraction purified by chromatography carried out under the conditions described in Example 5.2 showed that this preparation had a purity level at least equal to that of the preparation conventionally obtained by ultracentrifugation, and that it is free of contaminating proteins or of contaminating nucleic acids.

5.4. Purification of Intracellular Adenovirus by Strong Anion Exchange.

This example illustrates how an adenovirus comprising in its genome a heterologous nucleic acid sequence may be directly purified in a single ion-exchange chromatography step has from a lysate of encapsidation cells producing the said virus.

In a typical purification experiment, an adenovirus comprising in its genome a heterologous nucleic acid sequence encoding the β-gal protein is purified by chromatographing in the system described in Example 5.1 (FineLine Pilot 35 column, Pharmacia, 100 ml of Source 15Q resin), 450 ml (that is to say $2.5 \times 10^{14}$ particles) of concentrated lysate of a cell culture harvested 3 days post-infection by chemical lysis (1% Tween-20). The viral particle peak collected after chromatography (110 ml) contained $2.15 \times 10^{14}$ particles, which indicates a particle yield of 86%. After this purification step, the fraction collected had a viral particle purity greater than 98% during the chromatographic analysis under the conditions described in 5.2. Electrophoretic analysis of the adenoviral fraction purified by chromatography carried out under the conditions described in Example 5.2 showed that this preparation had a level of purity at least equal has that of a preparation conventionally obtained by ultracentrifugation, and that it lacks contaminating proteins or contaminating nucleic acids.

5.5. Purification of the Virus by Ultrafiltration and Ion-Exchange Chromatography on Various Columns.

This example illustrates how the adenovirus contained in the concentrate may be directly purified and in a single ion-exchange chromatography step using a gel different from the Source 15 Q support, while working on the same separation principle, the anion exchange by interaction with the quaternary amine groups of the matrix.

In a typical experiment for purification of the adenovirus, various recombinant adenoviruses (encoding βGal, apolipoprotein AI and TK) were purified by chromatography on a Source Q30 gel column following the protocol described in Example 5.1. The results obtained show that the Source Q30 gel makes it possible to obtain viral preparations of a purity of the order of 85%, with a yield of between 70 and 100%. In addition, the results obtained show that Q30 possesses, for the purification of adenovirus, an efficiency (expressed by the number of theoretical plates) of 1000 and a (maximum quantity of virus which may be chromatographed without the peaks becoming altered) of 0.5 to $1 \times 10^{12}$ vp per ml. These results show that the Source Q30 gel may therefore be suitable for the purification of recombinant adenoviruses, even though its properties remain inferior to those of Source Q15 (purity of the order of 99%, efficiency of the order of 8000 and capacity of the order of 2.5 to $5 \times 10^{12}$ vp per ml).

In another typical adenovirus purification experiment, a β-Gal adenovirus is purified by chromatography on a MonoQ HR 5/5 column using the procedure described in Example 5.1. The chromatographic image corresponding to the ultrafiltration retentate and to the purified viral preparation thus obtained is illustrated in FIG. 8.

In another typical adenovirus purification experiment, a β-Gal adenovirus is purified by chromatography on a Poros HQ/M column according to the procedure described in Example 5.1. The chromatographic image corresponding to the ultrafiltration retentate and to the purified viral preparation thus obtained is illustrated in FIG. 9.

Example 6

Purification of the Virus by Ultrafiltration and Gel Permeation

This example illustrates how the adenovirus contained in the concentrate (ultrafiltration retentate) may be purified directly by gel permeation chromatography, with very high yields.

6.1. Procedure

200 µl of the ultrafiltration retentate obtained in Example 4 (that is to say 1.3 mg of proteins) are injected into an HR 10/30 column (Pharmacia) filled with Sephacryl S-1000SF (Pharmacia) equilibrated for example in PBS buffer, pH 7.2 containing 150 mM NaCl (buffer C). The species are fractionated and eluted with buffer C at a flow rate of 0.5 ml/min and detected at the outlet of the column by UV at 260 nm. Alternatively, it is possible to use, under the same operating conditions, a column filled with Sephacryl S-2000, which allows a better resolution than the column Sephacryl S-1000HR for particles of 100 nm to 1000 nm.

The resolution of the two gel permeation chromatographic systems described above may be advantageously enhanced by chromatographing the ultrafiltration supernatant (200 µl) on a system of 2 HR 10/30 columns (Pharmacia) coupled in series (Sephacryl S-1000HR or S-2000 column followed by a Superdex 200 HR column) equilibrated in the buffer C. The species are eluted with the buffer C at a flow rate of 0.5 ml/min and detected by UV at 260 nm. In this system, the viral particle peak is very clearly better separated from the lower-molecular weight species than in the system comprising a Sephacryl S-1000 HR or Sephacryl S-2000 column alone.

In a representative experiment, an ultrafiltration retentate (200 µl, 1.3 mg of proteins) was chromatographed on a system of 2 Sephacryl S-1000HR-Superdex 200 HR 10/30 columns (FIG. 10). The chromatographic peak containing the viral particles was collected. Its retention time coincides with the retention time obtained with a preparation of viral particles purified by ultracentrifugation. The viral particle peak collected after chromatography (7 ml) contained 28 µg of proteins and $3.5 \times 10^9$ PFU. Its analysis by analytical ion-exchange chromatography under the conditions described in Example 5.2 shows the presence of a contaminating peak which is more strongly retained on the analytical column, whose surface area represents about 25% of the surface area of the viral peak. Its 260 nm/280 nm absorbance ratio which has a value of 1.86 indicates that this contaminating peak corresponds to nucleic acids. The viral particles were therefore purified about 50 fold (in terms of quantity of proteins) and the purification yield is 85% as PFU.

Alternatively, it is possible to chromatograph the preparations of viral particles (ultrafiltrates or fractions at the outlet of an anion-exchange chromatography) on a TSK G6000 PW column (7.5×300 mm; TosoHaas) equilibrated in the buffer C. The species are eluted with the buffer C at a flow rate of 0.5 ml/min and detected in UV at 260 nm. Likewise, it may be advantageous to increase the resolution of the chromatographic system, in particular to increase the separation of the viral particle peak from the lower-molecular weight species, by chromatographing the ultrafiltration supernatant (50 to 200 µl) on a system of 2 columns coupled in series [TSK G6000 PW column (7.5×300 mm) followed by a Superdex 200 HR column] equilibrated in the buffer C. The species are eluted with the buffer C at a flow rate of 0.5 ml/min and detected in UV at 260 nm.

Example 7

Purification of the Virus by Ultrafiltration, Ion Exchange and Gel Permeation

The viral particle fraction derived from the anion-exchange chromatography (Example 5) may be advantageously chromatographed in one of the gel permeation chromatographic systems described above, for example with the aim of further enhancing the level of purity of the viral particles, but also mainly with the aim of packaging the viral particles in a medium compatible with or adapted to subsequent uses of the viral preparation (injection, . . . )

What is claimed is:

1. A method for producing recombinant adenoviruses, the method comprising introducing adenoviral DNA into a culture of encapsidation cells, and harvesting adenoviruses following their release into culture supernatant without lysis of the encapsidation cells by an external factor.

2. The method according to claim 1, wherein the harvesting is performed when at least 50% of the adenoviruses have been released into the supernatant.

3. The method according to claim 1, wherein the harvesting is performed when at least 70% of the adenoviruses have been released into the supernatant.

4. The method according to claim 1, wherein the harvesting is performed when at least 90% of the adenoviruses have been released into the supernatant.

5. The method according to claim 1, wherein the harvesting is by ultrafiltration.

6. The method according to claim 5, wherein the ultrafiltration is tangential ultrafiltration.

7. The method according to claim 5, wherein the ultrafiltration is performed on a membrane having a cut-off of less than 1000 kDa.

8. The method according to claim 1, wherein the harvesting is by anion-exchange chromatography.

9. The method according to claim 8, wherein the anion-exchange chromatography is performed on a strong anion-exchange resin.

10. The method according to claim 9, wherein the strong anion-exchange resin is selected from the group consisting of Source Q, Mono Q, Q Sepharose, Poros HQ, Poros QE, a Fractogel TMAE and Toyopearl Super Q.

11. The method according to claim 1, wherein the harvesting is by gel permeation chromatography.

12. The method according to claim 11, wherein th gel permeation chromatography is performed on a support selected from the group consisting of Sephacryl S-500 HR, Sephacryl S-1000 SF, Sephacryl S-1000 HR, Sephacryl S-2000, Superdex 200 HR, Sepharose 2B, 4B or 6B and TSK G6000 PW.

13. The method according to claim 1, wherein the harvesting is by ultrafiltration followed by anion-exchange chromatography.

14. The method according to claim 13, wherein the harvesting is by ultrafiltration followed by anion-exchange chromatography and then gel permeation chromatography.

15. The method according to claim 1, wherein the encapsidation cell transcomplements adenovirus E1 functions.

16. The method according to claim 15, wherein the encapsidation cell transcomplements adenovirus E1 and E4 functions.

17. The method according to claim 15, wherein the encapsidation cell transcomplements adenovirus E1 and E2a functions.

18. The method according to claim 15, wherein the cell is an embryonic human kidney cell, a human retinoblast or a cell from a human carcinoma.

19. The method according to claim 10, wherein the strong anion exchange resin is Source 15 Q.

* * * * *

UNITED STATES PATENT AND TRADEMARK OFFICE
CERTIFICATE OF CORRECTION

PATENT NO.    : 6,485,958 B2
DATED         : November 26, 2002
INVENTOR(S)   : Francis Blanche et al.

It is certified that error appears in the above-identified patent and that said Letters Patent is hereby corrected as shown below:

<u>Title page,</u>
Add Item: -- [73] Assignee: Gencell S.A. --

Signed and Sealed this

Fifth Day of August, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 25
<212> TYPE: DNA
<213> ORGANISM: Adenovirus

<400> SEQUENCE: 1
taattacctg ggcggcgagc acgat                                        25

<210> SEQ ID NO 2
<211> LENGTH: 25
<212> TYPE: DNA
<213> ORGANISM: Adenovirus

<400> SEQUENCE: 2
accttggatg ggaccgctgg gaaca                                        25

<210> SEQ ID NO 3
<211> LENGTH: 25
<212> TYPE: DNA
<213> ORGANISM: Adenovirus

<400> SEQUENCE: 3
tttttgatgc gtttcttacc tctgg                                        25

```
<210> SEQ ID NO 4
<211> LENGTH: 25
<212> TYPE: DNA
<213> ORGANISM: Adenovirus

<400> SEQUENCE: 4
cagacagcga tgcggaagag agtga                                        25

<210> SEQ ID NO 5
<211> LENGTH: 25
<212> TYPE: DNA
<213> ORGANISM: Adenovirus

<400> SEQUENCE: 5
tgttcccagc ggtcccatcc aaggt                                        25

<210> SEQ ID NO 6
<211> LENGTH: 25
<212> TYPE: DNA
<213> ORGANISM: Adenovirus

<400> SEQUENCE: 6
aaggacaagc agccgaagta gaaga                                        25

<210> SEQ ID NO 7
<211> LENGTH: 25
<212> TYPE: DNA
<213> ORGANISM: Adenovirus

<400> SEQUENCE: 7
ggatgatatg gttggacgct ggaag                                        25

<210> SEQ ID NO 8
<211> LENGTH: 25
<212> TYPE: DNA
<213> ORGANISM: Adenovirus

<400> SEQUENCE: 8
agggcggatg cgacgacact gactt                                        25
```